United States Patent [19]

Ebersole et al.

[11] Patent Number: 4,985,128
[45] Date of Patent: Jan. 15, 1991

[54] PROCESS FOR PREPARATION OF ELECTROPHORESIS

[75] Inventors: Richard C. Ebersole, Wilmington; Robert P. Foss, Hockessin, both of Del.

[73] Assignee: E. I. Du Pont de Nemours and Company, Wilmington, Del.

[21] Appl. No.: 463,899

[22] Filed: Jan. 9, 1990

Related U.S. Application Data

[60] Continuation of Ser. No. 235,399, Aug. 24, 1988, abandoned, which is a division of Ser. No. 928,154, Nov. 7, 1986, Pat. No. 4,840,756, which is a division of Ser. No. 604,586, Apr. 27, 1984, Pat. No. 4,704,198.

[51] Int. Cl.$^5$ .............................................. C08F 2/46
[52] U.S. Cl. ...................................... 204/182.8; 522/3
[58] Field of Search ........................... 204/182.8; 522/3

[56] References Cited

U.S. PATENT DOCUMENTS

| | | | |
|---|---|---|---|
| 2,448,594 | 9/1948 | Hillier | 430/296 |
| 2,524,862 | 10/1950 | White | 264/22 |
| 3,455,337 | 7/1969 | Cook | 428/36 |
| 3,578,604 | 5/1971 | Uriel | 252/316 |
| 3,788,950 | 1/1974 | Hicks et al. | 195/103.5 R |
| 3,876,446 | 4/1975 | Bleckmann | 264/22 |
| 3,993,551 | 11/1976 | Assarsson | 204/159.14 |
| 4,113,912 | 9/1978 | Okita | 428/290 |
| 4,115,339 | 9/1978 | Restaino | 524/814 |
| 4,137,969 | 2/1979 | Phalangas et al. | 166/274 |
| 4,188,370 | 2/1980 | Boschetti | 210/198 |
| 4,189,370 | 2/1980 | Boschetti | 204/299 R |
| 4,192,727 | 3/1980 | Ward | 522/3 |
| 4,218,356 | 8/1980 | Evans | 260/29.6 TA |
| 4,248,685 | 2/1981 | Beede | 522/84 |
| 4,264,711 | 4/1981 | Greeneich | 430/942 |
| 4,333,972 | 6/1982 | Kesting | 427/246 |
| 4,457,817 | 7/1984 | Bobeth et al. | 8/115.52 |
| 4,594,064 | 10/1986 | Anderson | 425/145 |
| 4,695,354 | 9/1987 | Sugihara | 204/180.1 |

OTHER PUBLICATIONS

B. J. Radola, Ed., "Electrophoresis 1979", Walter De Gruyter, New York (1980), pp.79-94, B. J. Radola, A. Kinzkofer, and M. Frey in: R. C. Allen and P. Arnaud, Eds., Electrophoresis 1981, Walter De. Gruyter, New York (1981), pp. 181-189, A. Gorg, W. Postel, R. Westermeier, E. Gianazza, and P. G. Righetti, ibid., pp. 259-270.

Chapiro, "Radiation Chemistry of Polymer Systems," Interscience, New York (1962), pp. 323-328.

R. Assam and K. Singer, "Prep. Short Contrib.-Bratislava-IUPAC Int. Conf. Modif. Polym." 5th, 1, 143-148 (1979).

G. P. Korneeva, D. M. Margolin, E. B. Mamin and L. V. Chepel, "Radiats. Khim." 2, 275-277 (1973).

E. Collinson, F. S. Dainton, and G. S. McNaughton, "Faraday Soc. Trans.", 53, 476-488 (1957).

A. Chapiro, "Radiation Chemistry of Polymeric Substances," High Polymer Series, vol. XV, Interscience, New York, 1962, pp. 8-9.

J. D. Nordstrom, in R. Bakish, Ed., "Electron and Ion Beam Science and Tech., 4th Intl. Conf." the Electrochemical Socl. New York 1979, pp. 605-618.

*Primary Examiner*—John F. Niebling
*Assistant Examiner*—Isabelle R. McAndrews

[57] ABSTRACT

Describes a process for controlling the polymerization and cross-linked density of electrophoretic gel products useful for separation of bioorganic molecules, which process does not use initiators common to processes of the art. Electron beam polymerized gels afford the desired advantages of being ultra thin and having a high electrophoretic resolution with programmable porosity profiles.

5 Claims, 21 Drawing Sheets

Fig. 4. Effective %T vs Dose

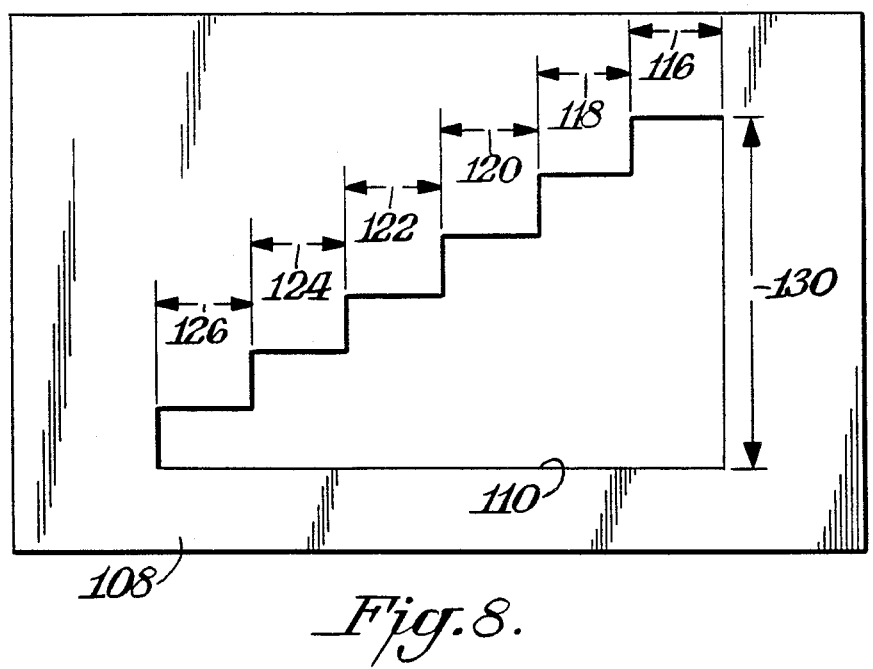
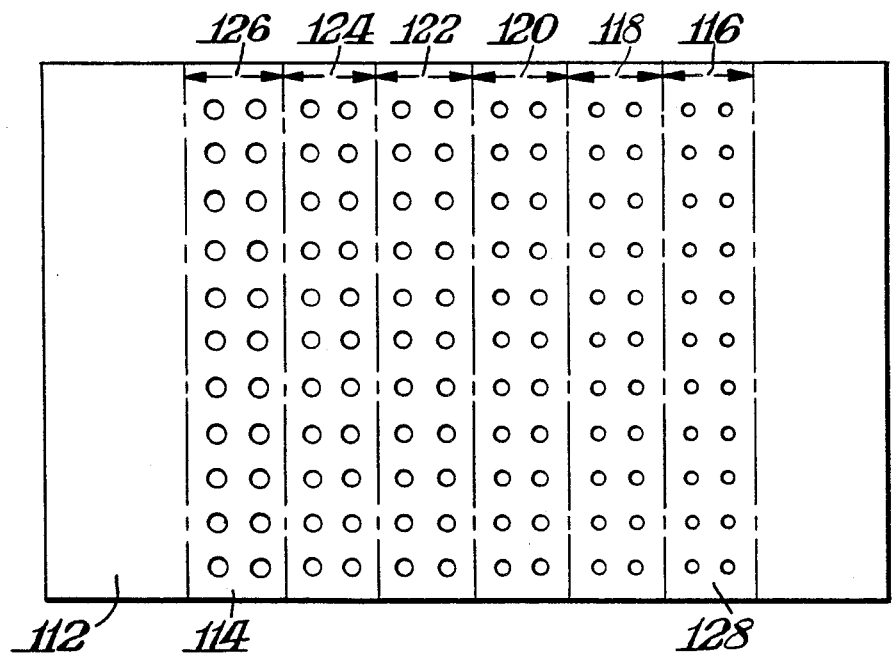

130

132

134

136

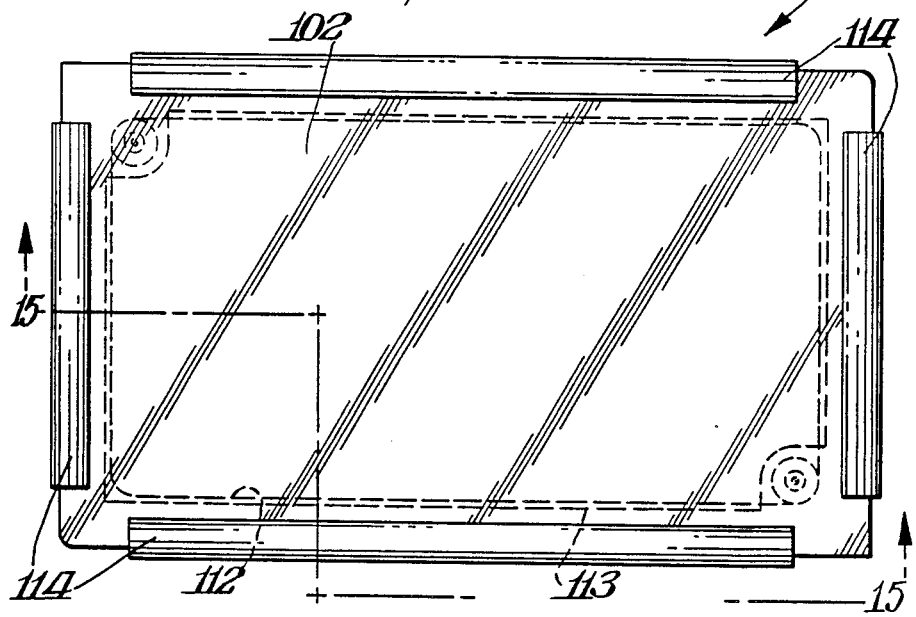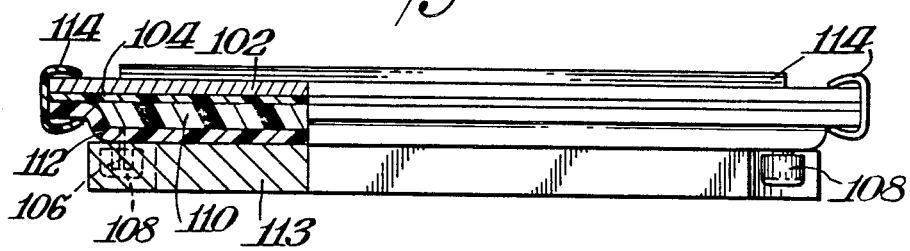

PROCESS FOR PREPARATION OF ELECTROPHORESIS

CROSS REFERENCE TO RELATED APPLICATION

This is application is a continuation of application Ser. No. 07/235,399 filed Aug. 24, 1988, now abandoned which is a division of 6/928,154 now U.S. Pat. No. 4,840,756 which is a division of 6/604,586 now U.S. Pat. No. 4,704,198.

FIELD OF THE INVENTION

This invention relates to electrophoretic gel products of controlled cross-link density, useful for separation of bioorganic molecules, and to controlled, radiative processes for their production, which do not use initiators common to processes of the art.

BACKGROUND OF THE INVENTION

Electrophoresis is based on the principle that charged molecules or substances will migrate when placed in an electric field. Since proteins and other biopolymers (e.g., DNA, RNA, enzymes and carbohydrates) are charged, they migrate at pH values other than their isoelectric point. The rate of migration depends, among other things, upon the charge density of the protein or biopolymer and the restrictive properties of the electrophoretic matrix. The higher the ratio of charge to mass the faster the molecule will migrate.

In theory, separation of different proteins could be readily achieved in free solution provided that the molecules differed sufficiently in their charge densities. However, in practice separations in free solution are difficult to achieve. Heat produced during electrophoresis can cause convection disturbances in the liquid medium distorting the protein bands. Recognition of the individual proteins is compromised because the bands are constantly broadened by diffusion. This continues even after electrophoresis has been stopped. Therefore, electrophoresis in free solution is rarely carried out. In practice various supporting media are currently used to minimize convection and diffusion, and to effect separation both on the basis of size and of molecular charge.

Many support media for electrophoresis are in current use. The most popular are sheets of paper or cellulose acetate, silica gels, agarose, starch, and polyacrylamide. Paper, cellulose acetate, and thinlayer silica materials are relatively inert and serve mainly for support and to minimize convection. Separation of proteins using these materials is based largely upon the charge density of the proteins at the pH selected.

On the other hand, starch, agarose and polyacrylamide gel materials not only minimize convection and diffusion but also actively participate in the separation process. These materials provide a porous medium in which the pore size can be controlled to approximate the size of the protein molecules being separated. In this way, molecular sieving occurs and provides separation on the basis of both charge density and molecular size.

The extent of molecular sieving is thought to depend on how closely the gel pore size approximates the size of the migrating particle. The pore size of agarose gels is sufficiently large that molecular sieving of most protein molecules is minimal and separation is based mainly on charge density. In contrast, polyacrylamide gels can have pores that more closely approximate the size of protein molecules and so contribute to the molecular sieving effect. Polyacrylamide has the further advantage of being a synthetic polymer which can be prepared in highly purified form.

The ability to produce a wide range of gel pore sizes and to form pore size gradients within the gel are additional advantages of polyacrylamide. Control over pore size enables mixtures to be sieved on the basis of molecular size and enables molecular weight determinations to be performed. These determinations are especially accurate if the proteins are coated with a detergent such as sodium dodecyl sulfate (SDS) which neutralizes the effects of molecular charge. This technique is referred to as SDS-PAGE electrophoresis.

PORE GRADIENT GELS

Polyacrylamide gels can be made with a gradient of increasing acrylamide concentration and hence decreasing pore size. These gels are now used extensively instead of single concentration gels, both for analysis of the protein composition of samples and for molecular weight estimation using SDS as a denaturing agent to render the proteins in a uniform charge environment. Step gradients in which gels of different concentration are layered one upon the other have been used. They tended to give artifactual multicomponent bands at the interface between layers. It is now common to use continuous acrylamide gradients. The usual limits are 3–30% acrylamide in linear or non-linear gradients with the particular range chosen depending upon the size of the proteins to be fractionated. During electrophoresis in gradient gels, proteins migrate until the decreasing pore size impedes further progress. Once this "pore limit" is approached the protein banding pattern does not change appreciably with time although migration does not cease completely.

One of the main advantages of gradient gel electrophoresis is that the migrating proteins are continually entering areas of gel with decreasing pore size such that the advancing edge of the migrating protein zone is retarded more than the trailing edge, resulting in a marked sharpening of the protein bands. In addition, the gradient in pore size increases the range of molecular weights which can be fractionated simultaneously on one gel. Therefore a gradient gel will not only fractionate a complex protein mixture into sharper bands than is usually possible with a gel of uniform pore size, but also can permit the molecular weight estimation of almost all the components.

Native proteins can also be analyzed on gradient gels using non-dissociating buffers.

Pore gradient gels are conventionally prepared by mixing high and low concentration monomer solutions in order to produce a concentration gradient of acrylamide in the gel molds. Using this type of approach both linear and non-linear gradient shapes can be prepared with respect to pore size along the length of the gel.

In addition to the gradient in acrylamide concentration, a density gradient of sucrose or glycerol is often included to minimize mixing by convective disturbances caused by the heat of polymerization. Some workers avoid the latter problem by including a gradient of polymerization catalyst to ensure that polymerization occurs first at the top of the gel and then proceeds to the bottom.

The polyacrylamide gel so prepared results from polymerization of acrylamide and simultaneous polymer cross-linking by bifunctional compounds such as N,N'-methylene-bis-acrylamide (BIS). The polymerization is normally initiated by either ammonium persulfate or riboflavin. Thermal polymerization with persulfate is accelerated by the addition of organic bases such as N,N,N',N'-tetramethylethylenediamine (TMEDA). Photochemical initiated polymerization by riboflavin requires visible or UV light. In all cases, oxygen inhibits the radical polymerization and monomer mixtures must be degassed prior to initiation.

The details of the preparation and the use of such gels for electrophoresis are generally and comprehensively reviewed by B. D. Hames in B. D. Hames and D. Rickwood, Eds., "Gel Electrophoresis of Proteins", pp. 1-89, IRL Press, Washington, D.C. (1981).

pH GRADIENT GELS (IEF)

Amphoteric materials (low molecular weight ampholytes) can be added to gel formulations. Following polymerization, the ampholyte materials migrate in the electric field according to their pI (isoelectric points) and come to rest in zones in the order of their pI. A pH gradient is thus produced in the gel.

The technique of isoelectric focusing makes use of these gels and takes advantage of the fact that each protein has a different pH at which it is electrically neutral - its isoelectric point (pI). Proteins are separated according to pI by electrophoresis on a gel in which a stable pH gradient has been generated, extending from a low pH at the anode to a high pH at the cathode. For example, if proteins are applied to the gel at a given pH location, those with a higher pI will bear a net positive charge and those with a lower pI will bear a net negative charge. When an electric field is applied, the positively charged molecules will move towards the cathode into a zone of increasing pH while the negatively charged molecules will move towards the anode into a zone of decreasing pH. When each protein reaches neutrality at its pI, it loses its electrophoretic mobility and becomes "focused" in a narrow zone.

Since diffusion is offset by the electric field, the bands do not broaden as in other separation methods. Isoelectric focusing can resolve proteins that differ in pI by as little as 0.01 pH units.

Further details of IEF separations are described by B. An der Lan and A. Chrambach, in B. D. Hames and D. Rickwood, "Gel Electrophoresis of Proteins", pp. 157-186, IRL Press, Washington, D.C. (1981).

Note that much of the general literature describe gels of 500 $\mu$ to 1500$\mu$ thickness. However, selected works do disclose thin and ultrathin gels in the range of 20$\mu$ to 500$\mu$ thicknesses. B. J. Radola and references therein, in: B. J. Radola, Ed., "Electrophoresis '79", Walter De Gruyter, New York (1980), pp 79-94 discuss ultrathin-layer isoelectric focusing in 50-100$\mu$ polyacrylamide gels (no gradient) prepared by casting on silanized glass or polyester sheets. B. J. Radola, A. Kinzkofer, and M. Frey in: R. C. Allen and P. Arnaud, Eds., "Electrophoresis '81", Walter De Gruyter, New York (1981), pp 181-189 describe isoelectric focusing in ultrathin-layer (20-50$\mu$) polyacrylamide gels. No discussion appears as to the gel preparation. A. Gorg. W. Postel, R. Westermeier, E. Gianazza, and P. G. Righetti, ibid., pp. 259-270 also describe isoelectric focusing and gradient electrophoresis in 240-360$\mu$ thick polyacrylamide gels. The gels are cast vertically, one at a time, by gradient mixing of solutions to form the pore-size gradient. Advantages of ultrathin gels are discussed.

Gels prepared by any of the above processes can suffer from several disadvantages which can compromise their utility in polyacrylamide gel electrophoresis (PAGE) and in isoelectric focusing (IEF). Unreacted polymerization initiators which are present can react with biological molecules and cause distorted separations or sample decomposition. The initiators present can increase background staining and thus decrease contrast of background with sample spots. Accelerators (e.g. TMEDA, tetramethylethylenediamine) can react with protein samples; can adversely affect electric conductivity of the gel matrix; and in IEF, may locally distort the pH gradients.

Prior to complete polymerization, the monomer solutions for both thick and thin gel preparation can be subject to distortion by thermal convection, turbulent mixing and adverse capillary flow, all of which can distort or destroy the pore-size (concentration) gradient or gradient shapes. Such random errors reduce accuracy and reproducibility of gradient gels. Thick gels require longer separation times and higher power for separation which increases gel and sample heating. Both effects can cause sample distortion or decomposition. The gels are usually prepared in small batches and are subject to the usual variability of batch operations such as variable accuracy, reproducibility, and quality control.

The types of gels that can be prepared are limited. There is no "fine-tuning" control of these processes.

Numerous references further discuss modifications of the basic electrophoretic and isoelectric focusing gels. U.S. Pat. No. 3,578,604 discloses the preparation of non-gradient, acrylamide/agarose gels by casting in the presence of persulfate. The use of photocatalysis is disclosed by other art. The final gels were useful in electrophoretic separations. Similarly, U.S. Pat. Nos. 3,788,950 and 4,189,370 claim processes for preparing acrylamide gels (or modifications thereof) in which gel formation is photoinitiated.

In general, the electrophilic gels prepared using the various prior art methods suffer from many disadvantages. Among these, the presence of various initiators in a gel often caused random reactions of the initiator with free monomer, buffers or acrylamide polymer. Furthermore, the initiator or its by-products may react with the protein samples themselves, thereby distorting the electrophoretic results. Because of the ineffective mechanical blending of reagents and uncontrolled reactions, the gels produced by the techniques of the prior art are neither accurate nor are they highly reproducible. Another problem encountered with the prior art techniques is that because of the thermal convection, vibration, mixing and capillary action, it is relatively difficult to produce thin gels, i.e., those less than 500$\mu$ in thickness. Further, these prior art techniques tend to be relatively expensive since they are batch-type operations and labor-intensive.

RADIATION POLYMERIZATION

In order to compensate for these disadvantages other types of polymerization processes have been reported in the literature. These include both thermal and photopolymerization processes.

The present invention makes use of radiation polymerization to improve in the control of the polymerization process.

The use of ionizing radiation (i.e. electron beams, $\alpha,\beta$- and $\gamma$-rays, protons, x-rays) to polymerize acrylamide is known for solution and solid systems. Chapiro ("Radiation Chemistry of Polymer Systems", Interscience, N.Y. (1962) pp 323-328) reviewed the general literature up to 1961.

R. Azzam and K. Singer, *Prepr. Short Contrib.-Bratislava-IUPAC Int. Conf. Modif. Polym.*, 5th, 1, 143-148 (1979) discuss the effects of dose rate, added species, and gel formation on the yield and MW of polyacrylamide prepared by radiation-induced polymerization. The reaction was carried out in deoxygenated water with dose rates of approximately 5 Mrads/sec. The added species were primarily inorganic salts. G. P. Korneeva, D. M. Margolin, E. B. Mamin and L. V. Chepel, *Radiats. Khim.*, 2, 275-277 (1973) describe the use of 2.1 MeV electrons to prepare thin, pseudo-solid layers of polyacrylamide.

U.S. Pat. No. 3,993,551 discloses the radiation cross-linking of polyethylene oxide with at least another water soluble polymer in an aqueous system. The products are insoluble, hydrophilic gels which contain aqueous fluids and are useful as absorbing media. The preferred reaction uses 0.1 MeV to 20 MeV energy levels of radiation with total doses of 0.05 to 10 Mrads. One of the co-crosslinked, water soluble polymers is polyacrylamide. A variation in dose was noted to directly change polymer absorbency.

U.S. Pat. No. 4,113,912 discloses hydrophilic porous structures comprising a fluorocarbon resin structure containing a water-insolubilized polymer; in one case the latter polymer is polyacrylamide crosslinked to form a swollen gel. One process, claimed for producing the structures, utilizes ionizing radiation for the insolubilization. Electron beams at 1-12 Mrads dosage were used as the ionizing radiation. E. Collinson, F. S. Dainton, and G. S. McNaughton, *Faraday Soc. Trans.*, 53, 476-488 (1957) describe in detail the x-ray and γ-ray initiated polymerization of acrylamide in aqueous solution. The relationships of degree of polymerization (average) and of overall polymerization rate to initial monomer concentration and dose rate are described. The overall polymerization rate was found to be proportional to the square root of the dose rate. Oxygen was reported to inhibit the acrylamide polymerization. Further, polymerization was reported to continue following termination of irradiation.

A Chapiro, "Radiation Chemistry of Polymeric Substances", High Polymer Series, Vol. XV, Interscience, N.Y. 1962, pp 8-9 describes work done by General Electric Co. and High Voltage Engineering, Inc. utilizing a resonant transformer and an experimental conveyor belt system for sample irradiation. The dosage received by the sample depends on the beam current, the scan width (and rate), and the speed of the conveyor belt. J. D. Nordstrom, in R. Bakish, Ed., "Electron and Ion Beam Science and Technology—4th Intl. Conf.", The Electrochemical Soc., N.Y., 1970, pp 605-618, reports that A. S. Hoffman and D. E. Smith, ACS Philadelphia Local Section, Nov. 1965 studied the conversion of monomer to polymer and found that gel formation (by cross-linking) continues to increase with dose after all of the monomer is incorporated into the polymer.

None of the polymers so produced were useful as electrophoretic gel products and none were prepared in a controlled, precisely programmed fashion to provide a controlled porosity.

The prior art provides important insight into the chemical events which occur in radiation induced polymerizations. With respect to the invention described herein, the art is specifically helpful in two respects.

First, the similarities and differences between chemical and radiation induced polymerizations have been identified. For example, many of the reactions which occur in radiation induced polymerization are similar to those which take place with chemical initiators. However, there are important differences which are unique to radiation polymerization processes and can significantly alter the properties of the resulting polymers. For example, radiation induced chain-to-chain cross-linking, chain to monomer cross-links, and chain degradation are important competing reactions which normally cannot be achieved with conventional chemical induced polymerization processes. The physical properties of the resulting polymers are thus not identical and, in many instances, can be substantially different.

Secondly, the prior art provides examples of the reactivity of the acrylamide monomer to radiation. Much of that work has only been carried out for homopolymers where acrylamide is the only monomer. There is currently no precedent for this type of polymer being useful for electrophoretic resolution of biopolymers. Furthermore, the relationships established between radiation exposure and the various physical properties of the polymers are not applicable as a guide since there currently are no known theoretical or emperical relationships established between the parameters investigated in those papers and the electrophoretic properties of the resulting polymer solutions.

SUMMARY OF THE INVENTION

According to the present invention, a porous gel product useful for electrophoretic separations is obtained. This product is characterized by absence of an initiator or electron donor and is stable, reproducible and has a controlled electrophoretic porosity. The gel product consists essentially of polyacrylamide and water, but may also contain acrylamide, agarose, bisacrylamide, and other monomers or polymers. Buffers or ampholytes, detergents and solutes may also be included in the formulations. The formulations are polymerized and cross-linked in a defined manner which may be mathematically defined for a specific use. Gel products may vary in thickness from 50$\mu$ to 2 ml with the 100-300$\mu$ range being most preferred.

Preferably the gel product consists of an aqueous-swelled porous matrix formed from polymerized and cross-linked acrylamide monomers. The concentration of acrylamide monomers in the solutions from which gels are made is essentially from about 3% (weight/volume) to about 30% (weight/volume). The gel products may have length, width and thickness dimensions and the pore size of the gels may be in the form of a gradient, which may vary along any of these dimensions and may be in a linear, or a complex function of pore size.

According to the method of this invention, charged bioorganic molecules are electrophoretically separated using the gel product described below a sample of bioorganic molecules is placed on a thin plate of this gel product and a voltage is applied across a dimension of the product.

The gel product is prepared by forming a water solution of a mixture of from about 3% (weight/volume) to about 30% (weight/volume) of acrylamide monomer and a cross-linking agent comprising about 0% (weight/weight) to about 10% (weight/weight) of the total monomer, adding an aqueous buffer to the solution to adjust the pH and ionic strength, forming a solution into the shape of the desired gel product, and subjecting the solution to ionizing radiation to polymerize and cross-link the monomer solution. The cross-linking agent includes N,N'-(1,2-dihydroxyethylene)-bis-acrylamide, N,N'-methylene-bis-acrylamide (BIS), N,N'-diallyltartramide (DATD), ethylenediacrylate, and N,N'-bis-acrylylcystamine and other cross-linking monomers. For a given composition, the dose and dose rate of the ionizing radiation applied to the monomer solution is regulated to vary the gel porosity. The dose regulations is accomplished by modulating the radiation flux as a function of the length, width and thickness of the gel. The flux may be modulated for fixed sheet-like gels by a computer and microprocessor programmed, moving shutter or by electronically modulating or scanning the beam position. Alternatively, the radiation flux can be modified for continuous manufacture by conveying or moving individual gel molds or continuous or undivided gel compositions under screens, halftone filters, grids, or variable shaped apertures, which modulate the radiation dose. Alternatively, electronic modulation of the beam may also be used in the continuous process.

The gel products prepared in the manner described have many advantages, among these are enhanced electrophoretic properties. For example, the gradient can be versitally programmed and can be accurately and reliably reproduced. The gels are cleaner due to the absence of initiator. Furthermore, thinner gels are readily produced using the method of this invention as well as custom gels, i.e., gels having any pattern porosity profile desired. In general, cheaper gels may be produced because of the continuous process permitted by the method of this invention. The gels are safer and the user does not have to handle toxic acrylamide, only the packaged gel. Furthermore, the gels manufactured by this invention can enable the application of higher voltages with faster migration times. Additionally, the gel products of this invention have reduced endosmosis flow due to the reduced ionic content of the gel formulation.

BRIEF DESCRIPTION OF THE DRAWINGS

The detailed operation of the method described briefly above can be best understood by reference to the following drawings in which:

FIG. 7 is a top plan view of a stepped dose gradient slit;

FIG. 8 is a drawing illustrating the resulting gel porosity profile from the stepped dose gradient slit in FIG. 7;

FIG. 14 is a top plan view of a gel mold and film support assembled and mounted on an aluminum support;

FIG. 15 is a cross-sectional view in elevation taken along line 15—15 of FIG. 14;

DETAILED DESCRIPTION OF THE PREFERRED EMBODIMENT

Method of the Invention

The method of the invention which overcomes many of the difficulties experienced in the prior art, is the ability to produce an electrophoretic gel of a known porosity profile without the aid of chemical initiators. This invention utilizes ionizing radiation as a means for the initiation of radicals in the gel which in turn results in gel polymerization. The degree of polymerization and cross-linking of a given monomer formulation in turn defines the electrophoretic gel separation characteristics which are the key to protein separation in electrophoretic gels. This radiation polymerization technology enables the preparation of all types of polyacrylamide electrophoresis gels. This technology enables control over the porosity and electrophoretic properties of the resulting gel materials which to date has been unobtainable. Using this approach, different types of electrophoresis gels can be successfully developed for a broad range of analytical applications including pore gradient gels for molecular weight determination and pH gradient gels for resolution on the basis of molecular charge and isoelectric point.

Figure 1:
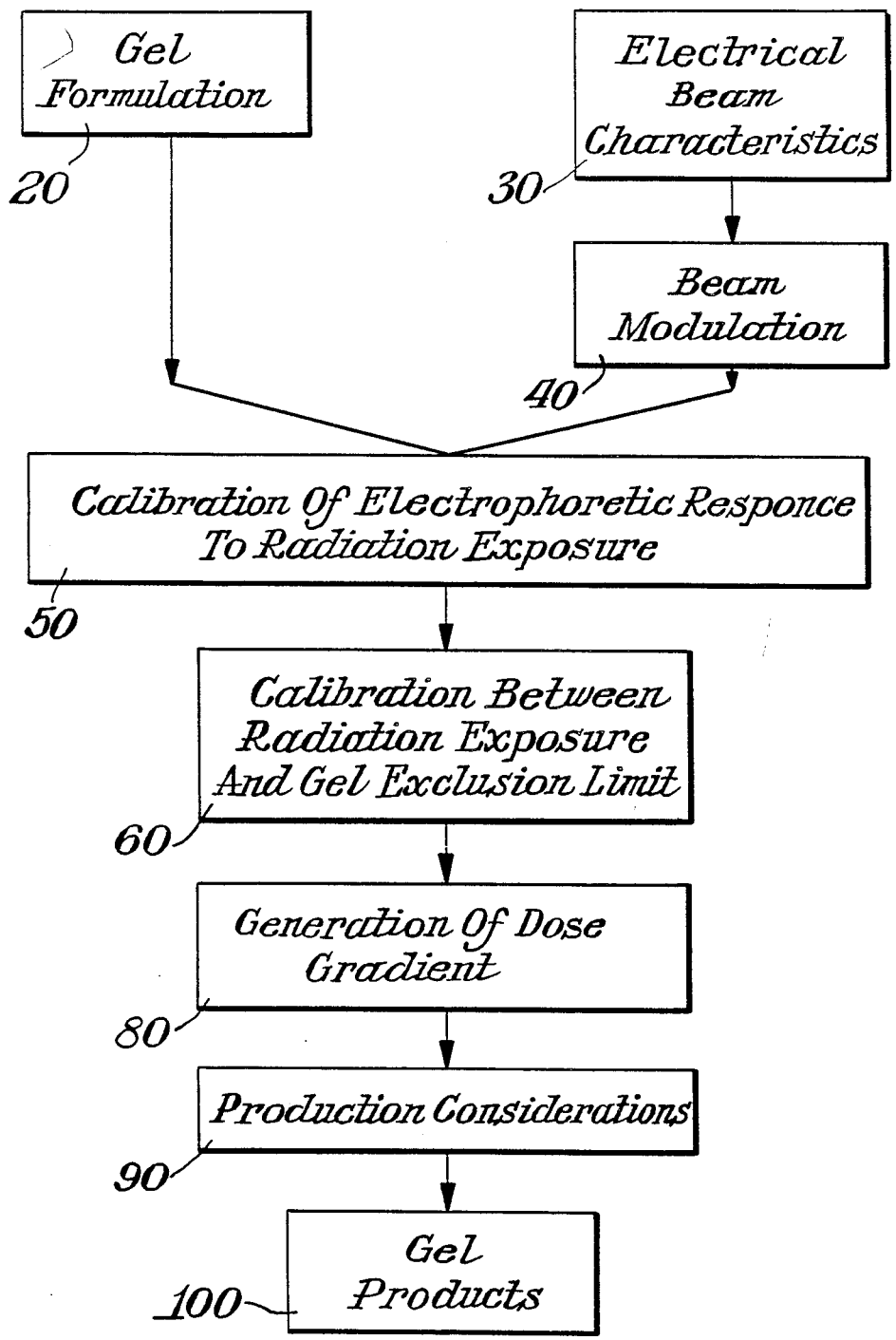
FIG. 1 is a block diagram of the method for generating electrophoretic gels via ionizing radiation.

Referring to FIG. 1, there is seen the steps of the method of this invention which may be used to produce electrophoretic gel products characterized by an absence of initiators which consists essentially of an aqueous-swelled porous matrix formed from polymerized and cross-linked monomers whereby the polymerization is initiated by radicals produced by ionizing radiation. This system illustrates the method of the invention and details those essential elements which must be considered when engaging in the manufacture of electrophoretic gel products via electron beam radiation. In FIG. 1, steps 20 through 100 specifically define these essential elements which in combination provides a unique approach in programming the porosity of a given gel composition. The steps are now described.

First the gel is formulated in step 20 by selecting the gel components which, depending upon the chemical compositions chose, influence the ability of the gel materials to polymerize and cross-link to yield the desired gel porosity and influence other separation characteristics. In order to establish a given radiation dose and dose rate combination during gel manufacturing the electron beam characteristics 30 must be known. To help direct the radiation to the target in order to establish the desired beam scanning patterns and dose profiles, beam modulation 40 techniques have been developed which can in turn allow for complex gel porosity patterns to be established. Once the gel formulation 20, electrical beam characteristics 30, and beam modulation 40 have been established, the next step involves the calibration of the selected electrophoretic gel compositions to the radiation system, which is termed calibration of electrophoretic response to radiation exposure 50.

A series of empirical calibration routines have been developed which characterize the relationships of the radiation dose to gel porosity. These relationships can then be used to determine other relationships which describes the effect of radiation dose to the molecular weight of proteins as a function of distance across a given gel of known composition. The calibration between radiation exposure and gel exclusion limit 60 can then be used for the generation of dose gradients 80 which are linear or non-linear, logrithmic, or complex providing the ability to program any combination of molecular weight or porosity versus distance relationship desired. This ability to control the gel porosity as a function of electron beam radiation produces a stable, accurate and reproducable gradient which can be easily adapted to a continuous manufacturing operation. Therefore, production considerations 90 are warranted. All of the above steps lead to the product 100 of this invention.

GEL FORMULATION 20

When considering manufacturing electrophoretic gels via ionizing radiation in accordance with this invention, the chemical composition considerations (Step 20) are important in order to achieve the desired porosity profile. For instance, the selection of gel materials influences gel characteristics such as the specific or non-specific binding of proteins or the electro endosmosis.

Acrylamide is the preferred and major monomer used in gel manufacturing; however, other water soluble monomers which can undergo radical initiated polymerization can be used. Other water soluble monomers may be co-polymerized with acrylamide to achieve desired properties. By the process disclosed, certain water soluble polymers can also be used in conjunction with the above monomers or directly to form gel products.

The concentration of the above described monomers in the initial gel formulation and in the final gel products may vary from about 3% wt/v to about 30% wt/v. This range is preferred for reasons of gel stability, strength and porous matrix properties. Gels with a low concentration of acrylamide are the most porous and pass large molecules easily. These are useful in IEF where no restriction of molecules is desired or in separation of large DNA fragments. Gels with a higher concentration of acrylamide are less porous and provide restrictive passage for higher resolution of low molecular weight materials.

Chemical cross-linking can occur in the gels by the presence of suitable polyunsaturated, functional acrylic or allylic compounds.

Compounds which act as suitable cross-linking agents include for example, N,N'-methylene-bis-acrylamide (BIS), N,N'-diallyltartramide (DATD), ethylenediacrylate, N,N'-bis-acrylylcystamine, N,N'-(1,2-dihydroxyethylene)bisacrylamide and TEOTA (polyoxyethyltrimethylolpropanetriacylate). BIS is preferred for reasons of reactivity, compatability and solubility but other cross-linking agents may be added to or used instead of the BIS. They are added to the initial gel formulation in concentrations of about 0% of the total monomer concentration (wt/wt); to about 10% of the total monomer concentration (wt/wt); the actual amount being determined by the degree of cross-linking required in the gel and may be determined empirically. The preferred range is about 2-7%. If these comonomers are added to the primary acrylamide composition, the concentration of acrylamide may not be less than about 50% of the total monomer concentration.

The total monomer concentration of the initial formulation (including cross-linking agent) on a weight percent/volume basis is expressed as % T. The concentration of the cross-linking monomer is expressed as a wt/wt percentage of the total monomer concentration and is called % C.

The gel formulations may be modified by the addition of polymeric materials compatible with the electrophoretic separation technique. Such compounds include but are not limited to agarose, agar-agar, and polyacrylamide (of varying molecular weights). The compounds may be added to modify viscosity, porosity and gel strength. They can be added to the formulation in concentrations ranging from about 0% wt/v to about 20% wt/v, the preferred range is determined empirically on the basis of each individual gel product.

Water soluble polymers that may be useful individually or as co-components in gel formulation include polyacrylamide, polyvinylpyrrolidone, polyethylene oxide, polymethylvinylether, polyvinyl-alcohol and agarose.

The initial gel formulation and hence the final gel itself may be further modified by the addition of varying concentrations of buffers, detergents, denaturants, ampholytes, and solutes. Buffer systems used are dependent on the final end use of the gel product. Typical examples of individual buffers, used in aqueous systems, include tris-(hydroxymethyl) aminomethane (TRIS)hydrochloric acid, citric acid, sodium hydrogen phosphate, and borates. Buffers may be used individually or in combination to insure proper buffering capacity and ionic strength. The concentrations and mixtures used in such buffer systems are selected on the basis of final end-use and are obvious to one skilled in the art. Details may be found in general references such as Hames and Rickwood.

Detergents may be added to gel formulations or directly to the bio-organic sample to be separated. In both cases, the detergent is added to solubilize the sample or to maintain a uniform charge to mass ratio so that samples separate solely on the basis of size. Detergents and their concentrations are selected empirically on the basis of gel product end-use and on the basis of sample type to be separated. Detergents which may be used include, for example, cetyltrimethyl ammonium bromide, cetylpyridinium chloride, deoxycholate, sodium dodecyl sulfate (SDS), polyethylene oxide sorbitan monooleate and ethoxylated octylphenols. General references such as Hames and Rickwood treat in detail the use of such detergents.

If the gel products are to be utilized for IEF separations, ampholytes must be added to the gel formulation. Ampholytes are amphoteric electrolytes added to IEF gels to generate the pH gradient necessary for IEF separation. The ampholytes sold commercially are generally complex mixtures of polybasic amines and polyacids. There are no limitations imposed by the instant invention on the type or concentration of ampholytes added to the instant gel products. References such as Hames and Rickwood clearly define the limitations of ampholytes inherent in all gel mixtures.

The initial gel formulations of the instant invention may or may not be degassed by inert gas (nitrogen, argon, helium, etc.) purging to remove dissolved oxygen prior to casting. Purging is preferred. The use of high intensity ionizing radiation for polymerization and cross-linking rapidly depletes dissolved oxygen and thus obviates the usual need to rigorously exclude oxygen from the initial gel formulation as long as sample preparation and exposure conditions remain constant and consistent. However, during irradiation a cover sheet or innet exposure chamber is necessary to prevent inhibition of polymerization due to atmospheric oxygen, which can be rapidly replenished by diffusion.

Once mixed, the initial gel formulation may be modified with further additives, if desired, and then is placed in a casting mold or simply between two cover sheets. Details of the casting are described later under production considerations 90.

Typical electron beam SDS-PAGE formulation for gradient and uniform gels are set forth in Example 1, and for IEF gels in Example 2.

EXAMPLE 1

The following example illustrates the preparation of electrophoresis gels using electron beam radiation.

Two stock reagent solutions were prepared. In solution I, purified acrylamide (20 gm) and N,N'-methylene-bis-acrylamide (1.0 gm) were dissolved in purified water (75 ml). Solution II was prepared by dissolving tris (hydroxymethyl) aminomethane (18.1 gm), sodium dodecyl sulfate (0.4 gm) in purified water (90 ml). The pH of the solution was adjusted to pH 8.8 using HCl and then made up to a final volume of 100 ml with purified $H_2O$.

The gel formulation was then prepared by mixing 3 parts of the acrylamide stock solution (I) with 1 part of the TRIS buffer solution (II) yielding the following composition:

| Acrylamide | 20% weight percent |
| Bisacrylamide | 5% by weight of the total monomer |
| TRIS Buffer | (.374 M) |
| Sodium Dodecylsulfate | 0.1% |

The gel formulation was then injected into molds and irradiated with 2 MeV electrons resulting in absorbed radiation doses ranging from 0.03 to 1.0 Mrads. The resulting gels on electrophoresis, exhibited porosities equivalent to conventional control gels prepared with monomer concentrations ranging from 5 to 28% T.

Exposures were performed at a distance of 60 cm using a dose rate of 0.00856 Mrads/sec using the computer driven shutter system.

EXAMPLE 2

5.9T, 3C FORMULATION FOR ELECTRON BEAM IEF GELS

48% Acrylamide Stock Solution:
23.30 g recrystallized acrylamide
0.70 g BIS
dilute to 50 ml with $H_2O$
5.9T, 3C IEF Solution:
 11 ml 48% acrylamide stock solution
 10 ml Servalyte 3–10 ampholytes*
 69 ml $H_2O$

* or a mixture of standard ampholytes solution to equal 10 ml.

ELECTRON BEAM CHARACTERISTICS 30 AND BEAM MODULATION 40

In order to successfully control the porosity across an electrophoretic gel product, certain electron beam characteristics must be considered as high-lighted below:

1. Beam Energy (Electron Volts e.v.)-Affects the penetration and vertical dose profile of ionizing radiation.
2. Incident Beam Power Flux (watts/cm$^2$)—beam output power.
3. Rate of energy absorption (Mrads/sec) in the sample is related to the mass thickness and beam energy and Power Flux obtained from dosimetry studies.
4. Uniformity of The Resultant Electron Beam Pattern—This must be taken into consideration in designing the slits, halftone filter or shutter program to compensate for non-uniformity.

Figure 2:
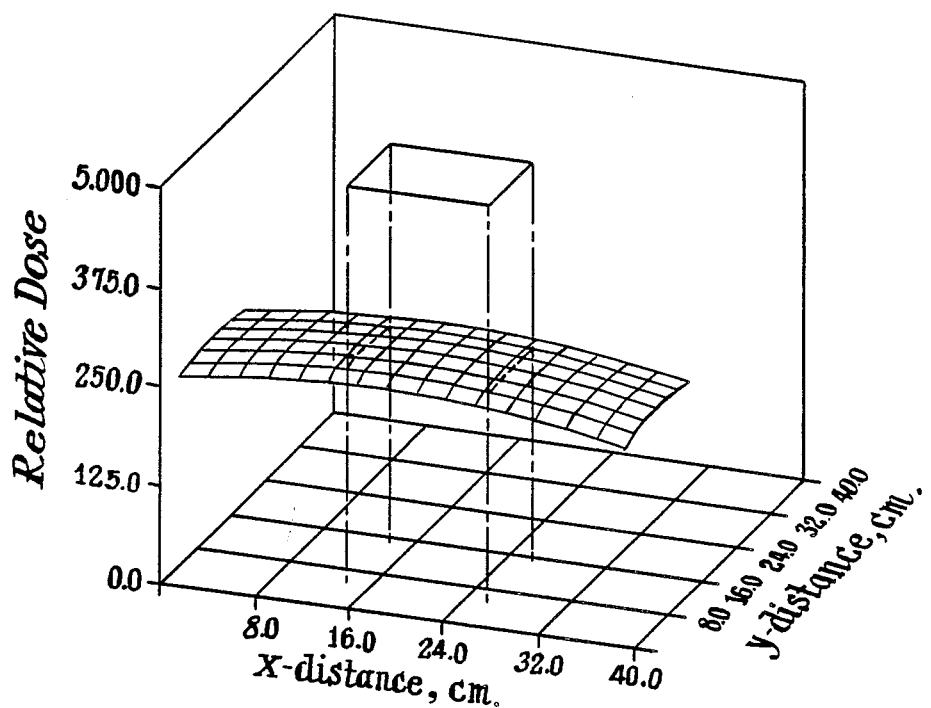
FIG. 2 is a drawing of an electron beam exposure pattern produced at 60 cm below the accelerator tube window of a 2MEV-G.E. Resonant Transformer.

The technique used to establish the above characteristics are well known in the art. For example devices such as a Faraday Cup, can be used to gather exposure distribution information as a function of a given X, Y coordinate. From this information a radiation exposure map can be generated as illustrated in FIG. 2. This exposure map, taken at a distance of 60 cm below the accelerator window, shows a uniform power flux (watts/cm$^2$) covering an area of 28 cm×25 cm in the center region of the beam. As will be described the electron beam is repetitively scanned in much the same manner as a TV raster scan, across the gel. This exposure map represents the output from a General Electric 2 MEV Resonant Transformer.

Although an electron beam was used as the source of radiation in this embodiment, other types of ionizing radiation such as positive ions, Alpha $\alpha$), Beta ($\beta$), Gamma ($\gamma$), and X-rays can be used.

Once the beam has been characterized, the dose of ionizing radiation can be regulated to vary the gel porosity. The dose regulation is accomplished by modulating the radiation flux (watts/cm$^2$) as a function of the length, width and thickness of the gel. The flux may be modified for a fixed sheet-like gel by a programmed shutter or by electronically modulating the beam position, as in raster scanning of a television picture. The instrument used to produce the ionizing radiation in this embodiment utilized a pulse-beam raster scanning technique and therefore, all calibrations were based upon this beam pattern. Where a conveyed web or moving sheet-like gel production operation is desired, such devices as halftone filters, grids, variable shaped apertures, or electronic modulation of the flux beam position can be incorporated to modify the flux. In a fixed gel production operation, a computer driven shutter, halftone filters, grids, or electronic modulation of the flux beam position can also be incorporated. More detailed discussion of these devices will be given in the section pertaining to the generation of the dose gradient.

EFFECTIVE POROSITY (T) AND DOSE (D) AS APPLIED TO GEL POLYMERIZATION VIA IONIZING RADIATION

Polyacrylamide electrophoresis gels are cross-linked polymer networks formed by polymerizing solutions normally containing 5–30% total acrylamide monomer in water. Normally 2–7% of the monomer is N,N'-methylene bisacrylamide (BIS). This is added to provide cross-links to the matrix. Normally the monomer is thermally polymerized to completion using standard persulfate initiator combinations, or photochemically using riboflavin. The restrictive nature of the gel is related to the percent of total monomer(%T) and the amount of cross-linker present via polymer density and degree of cross-linking.

Literature convention has defined the restrictive nature of a gel in terms of the percent total monomer containing 3% BIS polymerized in the gel. For example, a gel having a "20% T porosity" demonstrates the restrictive character of a gel formed by polymerizing to completion a solution of 20% total acrylamide to which 3% BIS had been added. Therefore, one refers to gels as having 10, 15, 20% T porosity depending on the composition.

This above convention works well in relating the electrophoretic response of the gel formulation since polymerization is assumed to approach completion. In the context of the present invention, the electrophoretic response can not be related directly to the acrylamide content or %T. This is because both degree and nature of the polymerization process is controlled by the radiation exposure. For example, using radiation polymerization, a range of porosity can be achieved with a given initial formulation by varying the range of electron exposure. The equivalent porosity of an electron radiation produced gel can be referred to as an equivalent effective %T, which will be termed T in the content of this disclosure.

Another term used in the disclosure, which is important to define, is the term dose (D), which refers to that quantity of radiation energy which is absorbed in an electrophoretic gel. The absorbed dose is defined as the fraction of energy absorbed in a given gel of a given thickness and the dose rate (DR) is the rate of energy absorbed in a given gel per unit time. For example, illustrated in Example #3 is a table which identifies the fraction of incident beam radiation energy absorbed for a given gel component of a given thickness.

EXAMPLE #3

THE FRACTION OF 2Mev ELECTRON RADIATION ENERGY ABSORBED IN A GIVEN TARGET MATERIAL OF A GIVEN THICKNESS

| Target Material | Mass Thickness (t) | Fraction of Energy Absorbed |
|---|---|---|
| Al Plate (25 mil) | .171 | .382 |
| Al Plate + Mylar (7 mil) | .178 | .420 |
| Al Plate + Mylar + Gel (12 mil) | .220 | .483 |
| Al Plate + Mylar + Gel (62.5 mil) | .380 | .718 |
| Al Plate + Mylar + Gel (125 mil) | .507 | .912 |
| Glass Plate (62.5 mil) | .349 | .720 |
| Glass Plate + Mylar (7 mil) | .367 | .748 |
| Glass Plate + Mylar + Gel (62.5 mil) | .526 | .927 |
| Glass Plate + Mylar + Gel (125 mil) | .684 | .995 |

The source of radiation used in the above tests was the General Electric G.E. 2 Mev Resonant Transformer.

The fraction of radiation energy absorbed (fa) by an electrophoretic gel 12 mils thick can be calculated by subtracting the total fraction of radiation energy absorbed for gel components consisting of; an aluminum plate (25 mils thick) and Mylar film (7 mils thick), from gel components consisting of an aluminum plate (25 mils thick), Mylar film (7 mils) and an electrophoretic gel (12 mls thick).

From Example #3, the fraction of energy absorbed is 0.419 and 0.483 respectively. Carrying out this subtraction would result in the following:

$$\begin{array}{r} .483 \\ -.419 \\ \hline .064 \end{array}$$

approximately 6% total energy absorbance is associated with the electrophoretic gel described.

The fraction of absorbed beam energy (fa) is related to the absorbed dose rate in Mrads/sec at 1.0 milliampere total accelerator beam current by the expression:

$$DR \text{Mrads/sec} = \frac{E_o \text{Mev} * I\mu \text{ amps/cm}^2 * fa(td)}{10 \text{ watt} \cdot \text{sec/Mrad} \cdot g * td \text{ g/cm}^2}$$

where Eo=energy of incident electron beam in MEV, I is incident beam current flux, Eo·I=power flux, fa=fraction of power absorbed, which is a function of sample mass thickness (td), where td is expressed as g/cm$^2$=d(g/cc)·t(cm); d=density; t=sample thickness. The total absorbed dose of energy in Mrads in the gel composition is dose rate (DR(Mrads/sec)) multiplied by time (sec) This absorbed energy or dose represents the energy associated with the initiation of free radicals in the polymerization process.

CALIBRATION OF ELECTROPHORETIC RESPONSE TO RADIATION EXPOSURE 50

Once the radiation source has been characterized, it is then necessary to calibrate the response of the selected gel formulation for a given dose and dose rate. This calibration of electrophoretic response 50 is very important in order to insure that the correct porosity will be produced from a given dose and dose rate combination. The first step in this process is to establish a mathematical relationship between porosity (T) and the Rf factor (Rf is defined as the protein migration distance divided by the distance for migration of a tracking dye which is not restricted by the gel) for a given protein in a given gel. This is accomplished empirically by conducting a comparative study of the migration of well-characterized reference proteins in uniform gels containing various amounts of monomers polymerized to completion using standard persulfate initiators as well as electron irradiation.

Figure 3:
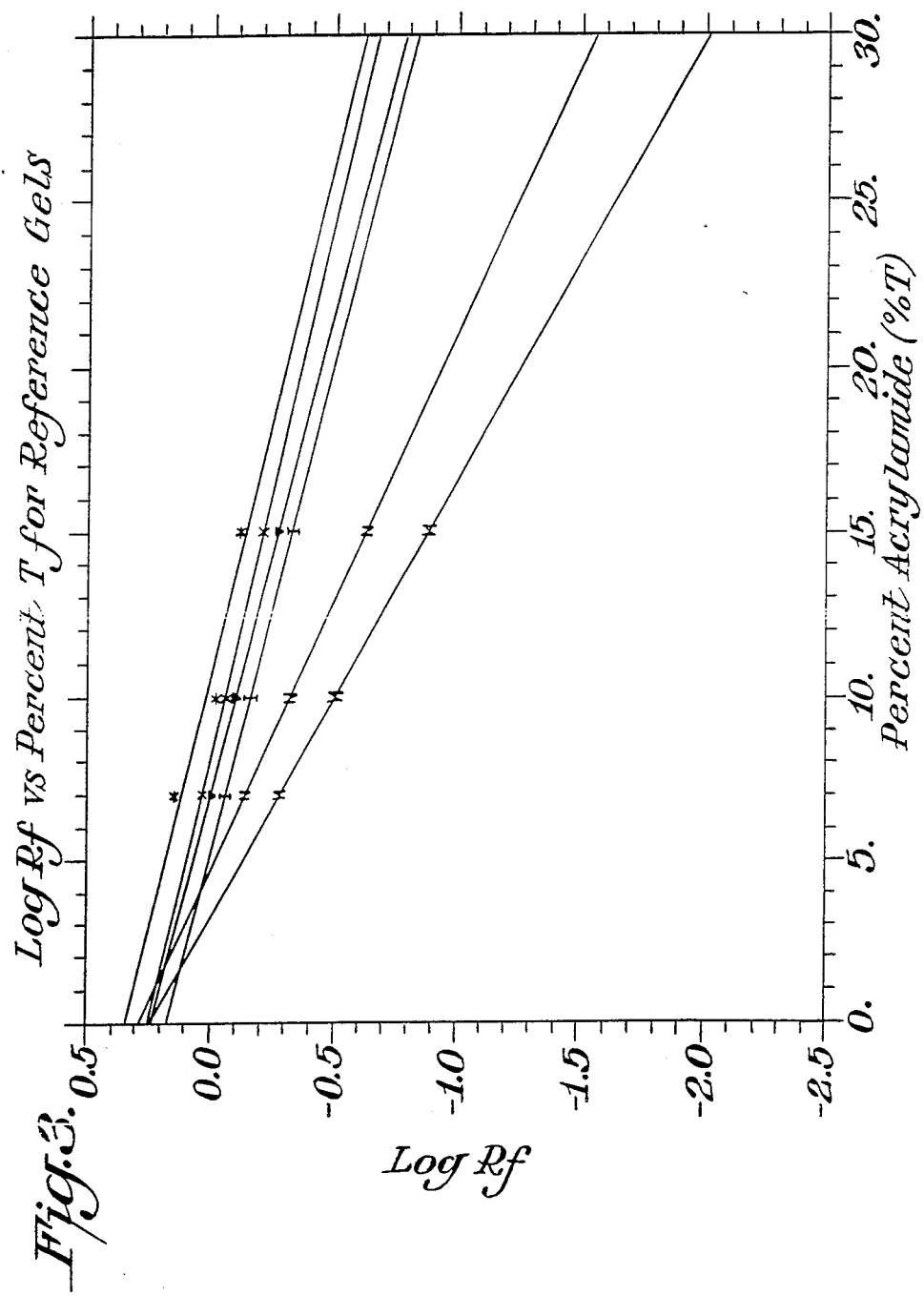
FIG. 3 is a drawing illustrating the relationship between Log Rf and Percent Acrylamide for various proteins with respect to tracking dyes.

A plot of log (Rf) versus %T is shown to give a family of linear curves, one for each different protein, as illustrated in FIG. 3. This relationship is essentially a measure of the drag imposed on the proteins by the restrictive gel material. Larger proteins are slowed more than small ones. The fitting constants relating log (Rf) to %T via:

$$\log(Rf) = C_1 + C_2 * (\%T)$$
$$\%T = a_1 + a_2 \log(Rf)$$

where $$a_1 = \frac{-C_1}{C_2} \text{ and } a_2 = \frac{1}{C_2}$$

were computed for various proteins in two types of electrophoretic gel formulations, i.e., 20T, 3C and 20T, 5C. These constants are illustrated in Example #4 below:

EXAMPLE #4

Fitting Constants Relating Effective
% T to Rf by the Function:
T = a$_1$ + a$_2$ log(Rf)

| # Protein | Mw | a$_1$ | a$_2$ | Remarks |
|---|---|---|---|---|
| Gel Type 20T, 3C: | | | | |
| 1 Insulin | 3000 | 10.638 | −27.146 | BRL |
| 2 Bovine Tripsine Inhibitor | 6200 | 8.118 | −32.288 | Standards |
| 3 Cytochrome-B(12300) Sysozyme (14300) | 13300 | 6.915 | −29.408 | |
| 4 β-Lactoglobulin | 18400 | 5.272 | −29.790 | Persulfate |
| 5 α-Chymotrypsinogen | 25700 | 4.676 | −16.252 | Polymerized (3% C) |
| 6 Ovalbumin | 43000 | 3.234 | −13.284 | |
| Gel Type 20T, 5C: | | | | |
| 1 Insulin | 3000 | 11.355 | −32.925 | BRL |
| 2 Bovine Tripsine Inhibitor | 6200 | 10.145 | −28.143 | Standards |
| 3 Cytochrome-B(12300) Lysozyme(14300) | 13300 | 9.226 | −23.594 | |
| 4 β-Lactoglobulin | 18400 | 8.359 | −19.093 | Radiation |
| 5 α-Chymotrypsinogen | 25700 | 7.455 | −13.339 | Polymerized |

EXAMPLE #4-continued

Fitting Constants Relating Effective
% T to Rf by the Function:
T = a$_1$ + a$_2$ log(Rf)

| # Protein | Mw | a$_1$ | a$_2$ | Remarks |
|---|---|---|---|---|
| 6 Ovalbumin | 43000 | 6.047 | −9.961 | (5% C) |
| 7 α-Lactalbumin | 14400 | 9.550 | −26.889 | PHL |
| 8 Tripsine Inhibitor | 20100 | 8.278 | −22.193 | Standards |
| 9 Carbonic Anlsydrase | 30000 | 6.397 | −18.899 | |
| 10 Ovalbumin | 43000 | 4.442 | −16.935 | Radiation |
| 11 Albumin (Human) | 67000 | 3.375 | −13.150 | Polymerized |
| 12 Phosphorylase-B | 94000 | 2.913 | −10.124 | (5% C) |

This study demonstrates the similarity between E-beam gels and those produced by normal literature procedures. It also provides standards by which porosity changes produced by radiation could be related to electrophoretic porosity values described in the literature.

Knowing the relationship of %T as a function of (Rf) for each protein one can calculate the effective %T (T) for any gel material given an Rf value for a protein transported electrophoretically in that material. Therefore, the effective porosity of a gel resulting from exposure to electrons can be measured and reported in terms of a T value using the relationship from the standards above.

Since an effective %T (T) is calculated for each protein, the effect of radiation on the matrix as it relates to movement of individual proteins can be checked by comparing differences between values calculated for each protein. Also, an average effective %T value can be calculated for each dose.

With this information established, the optimum conditions for gel preparation can be determined. Since polymerization, termination and cross-linking rates are dependent on radical concentration which is dose rate dependent, porosity (T) is expected to vary as a function of dose rate (DR) at constant dose.

A general expression describing effective %T as a function of both D and DR is:

$$T(D,DR) = F_1(DR) + F_2(DR) * D + F_3(DR)/D$$

$$\text{where } F_i(DR) = \sum_{n=0}^{3} k_{in} * (DR)^n$$

for $i = 1:3$.

Figure 4:
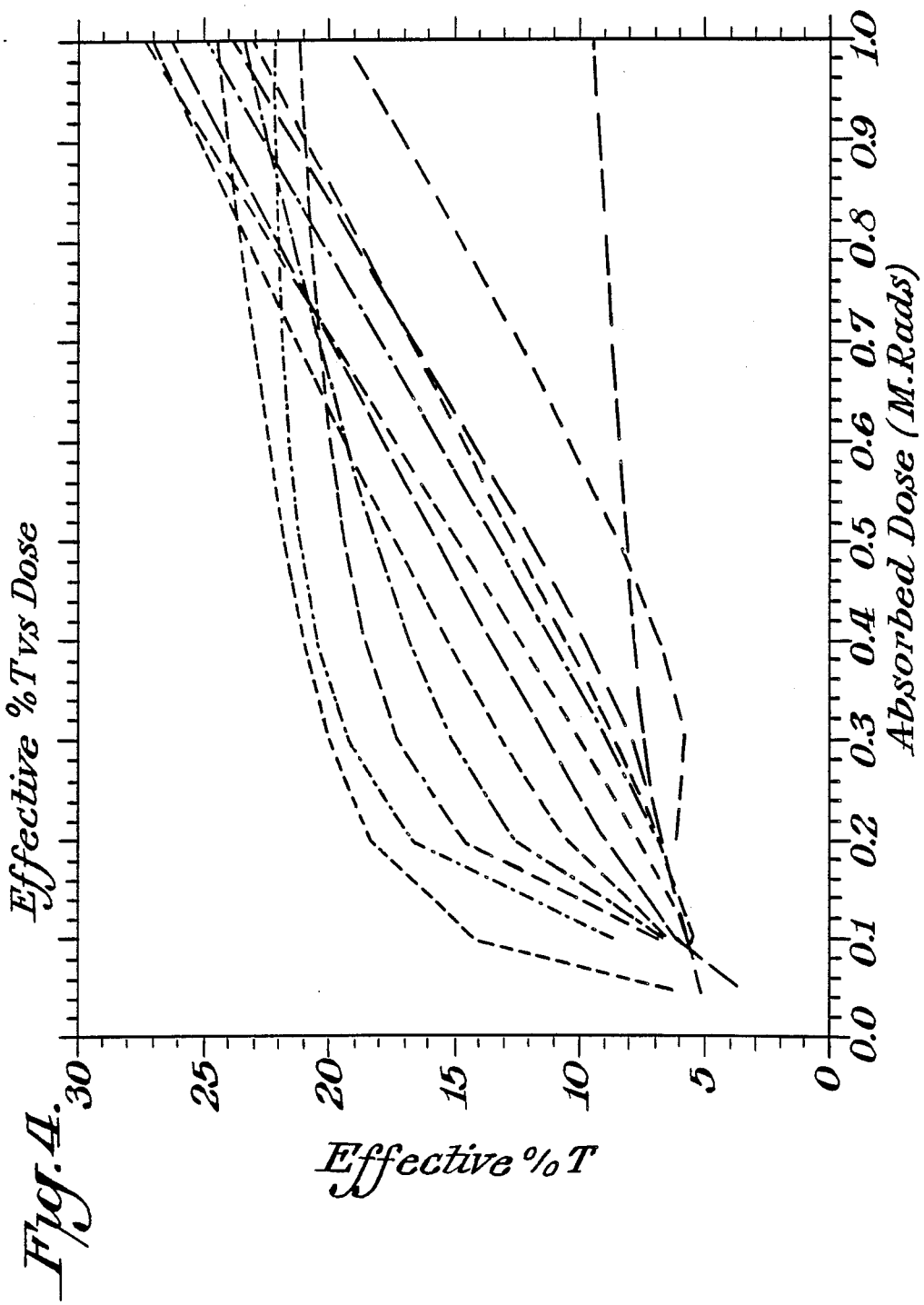
FIG. 4 is a drawing illustrating the effective porosity (T) versus Dose (D) as a function of Dose Rate (DR) for a given gel composition.

The values of $k_{in}$ were determined by fitting the above equations [F$_i$(DR)] to constants obtained from the data sets used to fit the function T versus dose for each DR for a given gel composition as illustrated in FIG. 4. These fitting constants F$_1$, F$_2$, and F$_3$ have been calculated for different gels at various dose rates and are listed in Example #5 below.

EXAMPLE #5

FITTING CONSTANTS FOR T VS D
AT VARIOUS DOSE RATES

| | Gel ID | Dose Rate | RMS | F$_1$(DR) | F$_2$(DR) | F$_3$(DR) |
|---|---|---|---|---|---|---|
| 1 | AV123 | 0.00994 | 1.336 | 21.28 | 3.989 | −0.752 |
| | AV13 | 0.00994 | 1.2071 | 22.65 | 2.303 | −0.837 |
| 2 | AV4 | 0.01988 | 0.430 | 24.97 | −1.175 | −1.617 |
| 3 | AV78 | 0.03021 | 1.287 | 22.27 | 0.439 | −1.545 |
| 4 | AV910 | 0.03976 | 0.887 | 15.95 | 8.460 | −1.014 |
| 5 | AV1112 | 0.05963 | 1.271 | 9.137 | 18.316 | −0.455 |
| 6 | AV56 | 0.07951 | 0.949 | 5.488 | 20.902 | −0.141 |

EXAMPLE #5-continued

FITTING CONSTANTS FOR T VS D AT VARIOUS DOSE RATES

| Gel ID | Dose Rate | RMS | $F_1(DR)$ | $F_2(DR)$ | $F_3(DR)$ |
|---|---|---|---|---|---|
| 7 AV1314 | 0.09416 | 0.988 | 2.140 | 25.09 | 0.095 |
| 8 AV1516 | 0.12712 | 0.414 | 1.287 | 23.38 | 0.182 |
| 9 AV1718 | 0.16478 | 0.504 | 1.675 | 21.13 | 0.178 |
| 10 AV1920 | 0.19538 | 1.227 | −2.154 | 25.24 | 0.755 |
| 11 AV21 | 0.22363 | 1.055 | −7.519 | 25.07 | 1.738 |
| 12 AV22 | 0.25894 | 0.312 | 7.295 | 2.440 | −0.173 |

This relationship allows a user to determine the resultant effective porosity (T) as a function of dose (D) and dose rate (DR) for a given gel. For example, referring to Example #5 if the effective porosity T is to be determined for Gel set 1 (I.D. AV123) with a dose rate of 0.00994 (Mrads/sec) the fitting constants associated with that gel and dose rate combination are $F_1(DR)=21.28$, $F_2(DR)=3.989$ and $F_3(DR)=-0.752$. Using the general expression describing effective %T as a function of dose and dose rate results in the following expression:

$$T(D,DR)=21.28+3.989*D-0.752/D$$

Therefore, T can be calculated for any desired dose (D) by simply inserting the value of dose into the above expression and solve for T. This relationship is used to calculate the required exposure parameters for producing desired gradients from calibration experiments run under different exposure conditions.

Figure 5:
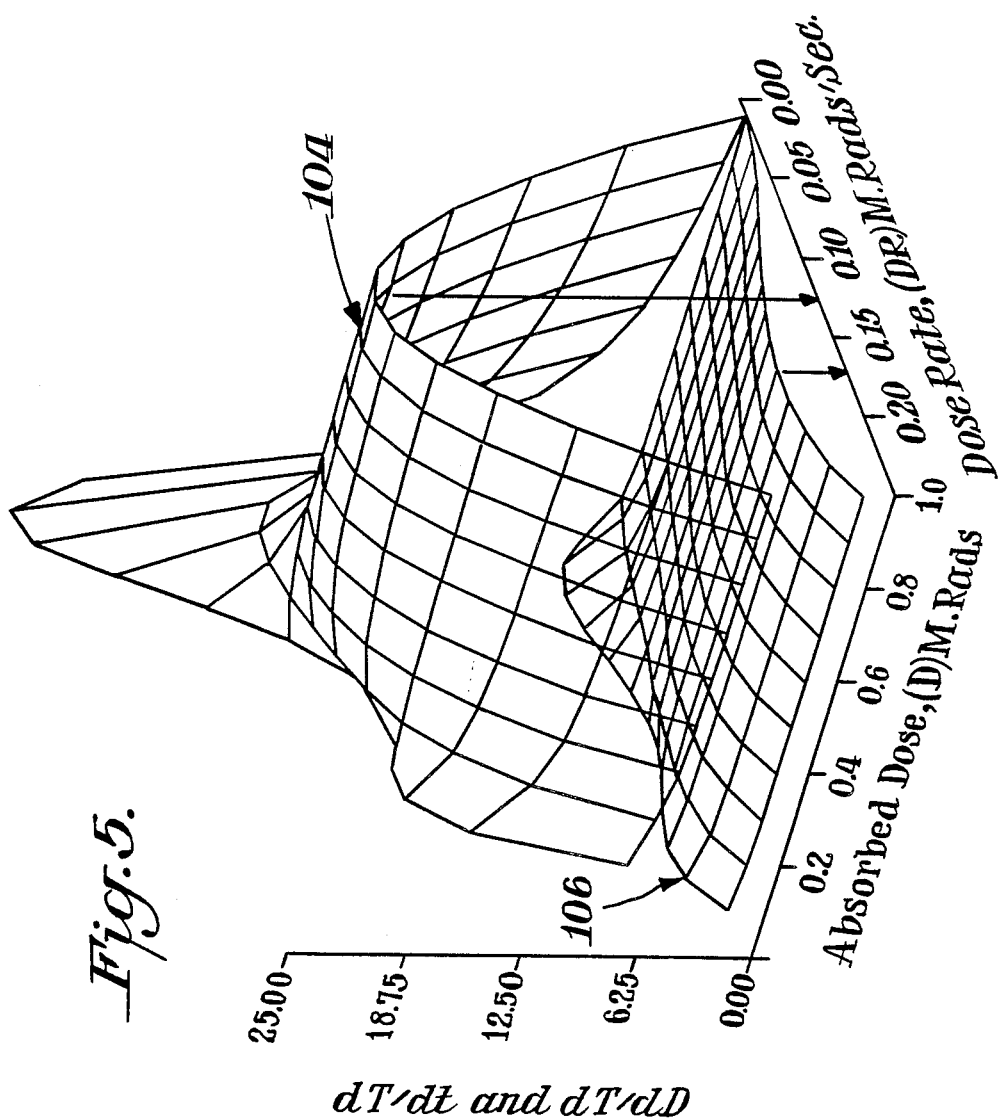
FIG. 5 is a drawing representing the rate of change of porosity (T) with respect to time and dose as a function of dose and dose rate.

FIG. 5 depicts the rate of change of porosity (T) with respect to time and dose as a function of dose and dose rate for a 20T, 5C acrylamide gels. A plot of change of T with respect to dose D, i.e. (dT/dD) as a function of dose (D) at each dose rate (dD/dt) is shown by the upper response surface 104 in FIG. 5. A maximum rate of increase in T occurs at a dose-rate of 0.13 Mrads/sec for gels having an initial 20T, 5C monomer composition. It is also seen from the upper surface 104 that the rate of change of T is essentially linear with respect to dose over the maximum dose rate range. This information defines the optimum conditions for the most efficient use of energy for preparing gradient gels.

By multiplying dT/dD by dose rate (dD/dt), one obtains the lower surface 106 in FIG. 5, which represents the rate of change of T with respect to time (dT/dt) for each dose rate. A maximum is obtained with this lower surface 106 at a dose rate of about 0.18 Mrads/sec and corresponds to the exposure conditions giving the maximum rate of gel production. As with the upper surface 104 it is seen that the response is relatively flat at optimum exposure conditions implying a broad exposure latitude. This is important in that it reduces error in gradient production that may result from beam intensity fluctuations. A linear rate-dose response is also apparent at the optimum conditions.

CALIBRATION BETWEEN RADIATION EXPOSURE AND GEL EXCLUSION LIMIT 60

In like manner to the above disclosure, a relationship between the exclusion limit molecular weight of a gel and the radiation exposure parameters can be established.

It is known from the literature and the standardization experiments conducted that a "limiting porosity" level (pore limit) can effectively be reached at which proteins of a given MW no longer can migrate. Since T (porosity) is related to dose there is expected to exist a corresponding "limiting dose" which will produce this limiting porosity. In order to produce standardized or calibrated MW gradients as function of migration distance, it is, therefore, necessary to determine this relationship between "limiting dose" and exclusion limit molecular weight.

Figure 6:
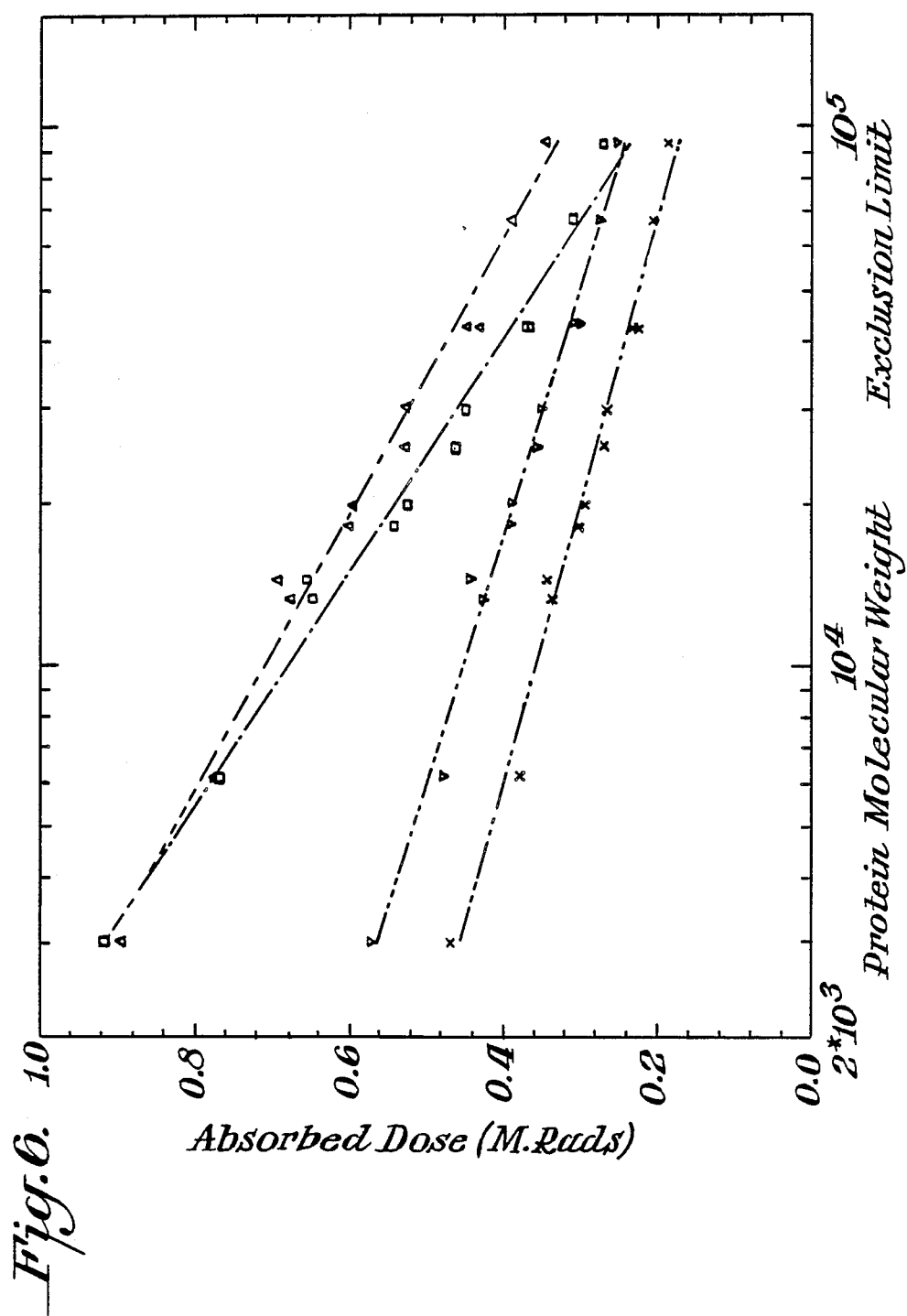
FIG. 6 is a drawing illustrating the limiting Dose (D) versus protein Molecular Weight exclusion limit ($MW_o$) for a given dose rate and gel composition.

Dose exclusion limit data from sets of equivalent gels were combined and various mathematical functions fit to the Dose versus MW distributions. A limiting dose (LDose) versus ln(MW) relationship $$LDose = C_1 + C_2 * \ln(MW)_o$$

gives the best fit for all sets at the optimum exposure conditions disclosed above. This relationship is shown in FIG. 6.

The constants $C_1$ and $C_2$ were determined for various dose rates and gel compositions as listed below:

| Gel Types | Dose Rate Mrads/sec | $C_1$ | $C_2$ |
|---|---|---|---|
| 20T 5C | .08 | 2.507 | −0.198 |
| 20T 5C | .13 | 2.266 | −0.169 |
| 30T 5C | .08 | 1.133 | −0.084 |
| 30T 5C | .13 | 1.314 | −0.0936 |

With this information the dose required to produce a desired protein molecular weight exclusion limit can be easily determined.

GENERATION OF DOSE GRADIENTS 80

The most common electrophoretic gel performance relationships used in the art is molecular weight versus distance and porosity versus distance profiles. The accuracy by which the porosity can be controlled as a function of distance across a gel is unique allowing for essentially a programmable profile which is dependent upon desired performance relationships. With the advent of porosity control via electron radiation a gel can be manufactured to the specific needs of a particular researcher.

The generation of the dose gradient incorporates a radiation flux modifying means for both fixed and conveyed or moving gels. This flux modifying means takes the form of moving shutters, screens, halftone filters, grids, variable shaped apertures or electronic modulation of the electron flux. A typical slit used for porosity gradient production is illustrated in FIG. 7, where depending upon the shape of the slit a given porosity profile is achieved. For example, using a stepped dose shaped slit as a mask 108 positioned above a gel carried on a conveyor moving under a radiation source, the radiation source would polymerize the gel 112 only in the regions of the mask which are open to the gel. If the gel were moved or conveyed relative to the mask and radiation source, certain regions of the gel would be exposed to the radiation for a longer length of time, i.e., a larger dose. Since dose is proportional to polymerization and cross-linking, which in turn is proportional to porosity, a pore gradient gel could be produced.

Figure 9A:
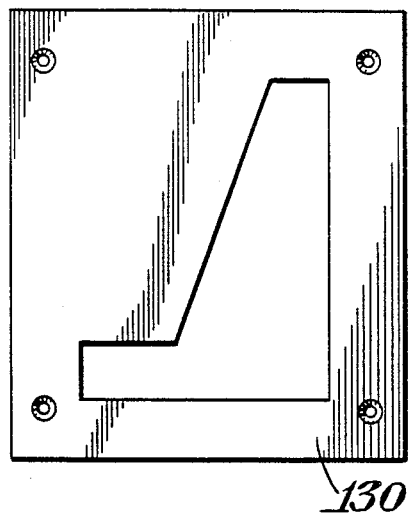
FIGS. 9a-d is a drawing illustrating different typical slits used for porosity gradients.
Figure 9B:
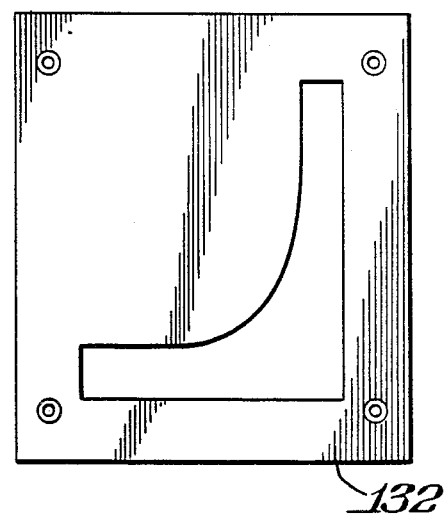
Figure 9C:
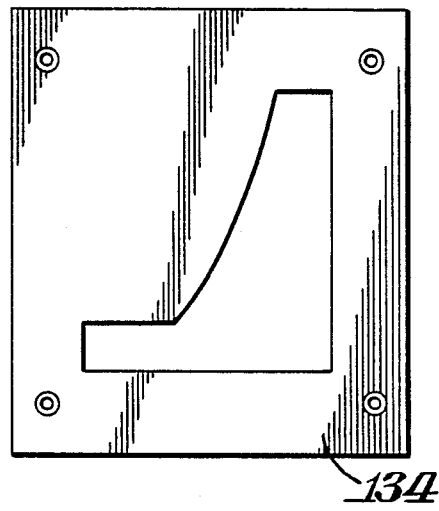
Figure 9D:
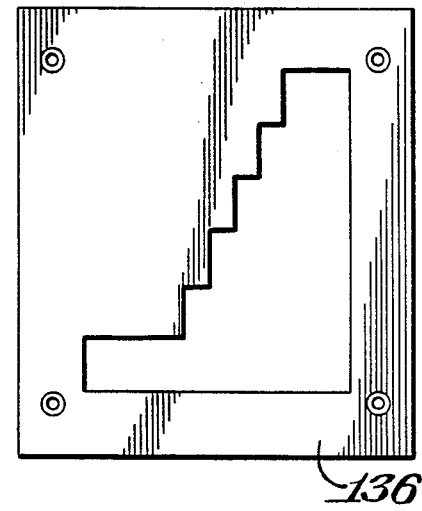

For example, in FIG. 7 & 8, an electrophoretic gel 112 exposed to radiation using the stepped dose gradient slit 110 would have porosity gradients in step fashion across the lanes 116 through 126. Lane 116 would have the highest degree of polymerization corresponding to a smaller pore size 128, since the vertical slit length 130 of lane 116 is the largest of the mask. Lane 126 would correspond to the least polymerized portion of the gel corresponding to a larger pore size 114. Other examples of different dose gradient masks are illustrated in FIG. 9a, b, c, d, such as a linear 130, polynomial 132, exponential 134, or stepped dose patterns 136.

Figure 10:
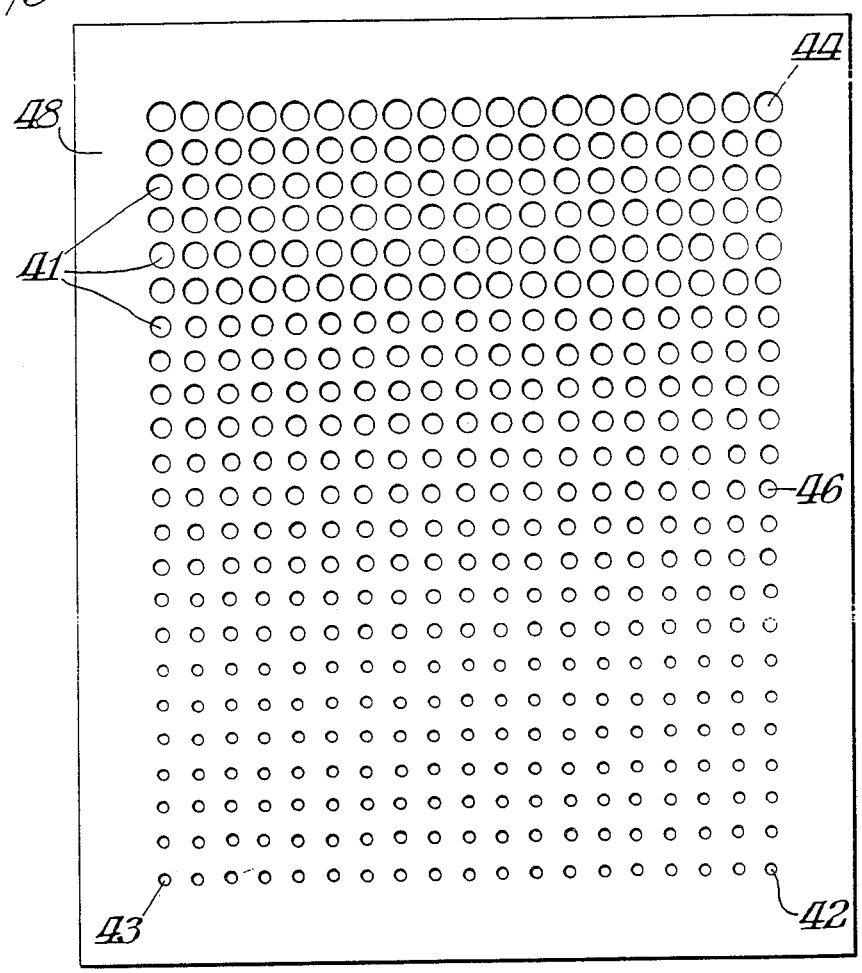
FIG. 10 is a drawing illustrating a halftone electron filter for a log gradient porosity profile.

Another type of flux modification device is the halftone electron filter or screen. An example of a halftone filter demonstrating a logrithmic gradient is illustrated in FIG. 10 and FIG. 11.

Figure 11:
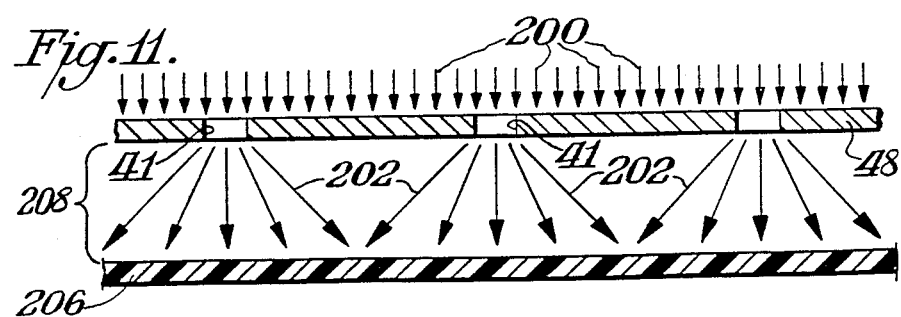
FIG. 11 is a drawing illustrating the electron scattering effect created by the halftone electronic filter illustrated in FIG. 10.

The halftone electron filter is essentially a plate of radiation absorbing material 48 FIG. 11 with holes 41 located across the surface of the plate. The thickness of the filter material is chosen so that it will totally absorb the electrons in the opaque regions. The holes are located at ¼ inch centers, but may be closer, relative to each other with their diameters incrementally varying across the length (from 44 to 42) of the plate. The hole diameters across the width of the plate (from 42 to 43) may be equal diameter in each row. With this configuration, row 44 will allow for the passage of more electrons than row 46. In turn, row 46 will allow the passage of more electrons than row 42. FIG. 11 illustrates the electron scattering effect of the halftone electron filter. Electrons 200 pass through the openings of the filter and are scattered 202 accordingly. If the target 206 is placed at the appropriate distance 208 from the filter 48, the diffuse transmitted beam will produce a uniform dose pattern over the target area. By placing a gel underneath a halftone filter and exposing the filter to a beam of electrons the effective porosity of the gel can be made to vary across its length according to the filter used. Therefore, a halftone filter in conjunction with a beam of electrons provides a convenient way of producing gradients or any other complex distributions across an electrophoretic gel. As with the variable slit, a conveyor can be used to produce an exposure gradient perpendicular to the travel direction. An advantage is that the beam cross section pattern can be of any shape (gaussian most likely) in the travel direction as in the case with many commercial accelerators. With a uniform beam, a filter, screen or grid can also be used in a fixed position relative to the sample to produce the desired 2-dimensional dose pattern.

For fixed or stationary gel exposure, porosity gradients can be created by the use of a programmable shutter assembly which moves across the gel at a prescribed speed. The speed of the shutter as it moves across a gel for a given dose, dose rate, and gel composition will determine the porosity profile. A detailed description of the shutter exposure system along with a continuous gel manufacturing process will be discussed in the section describing production considerations 90.

PRODUCTION CONSIDERATION 90

With the system calibrated and optimized in accordance with the discussion in the previous disclosure, it is entirely feasible to produce gels of a given porosity profile using the batch mode or continuous manufacturing operation.

Figure 12:
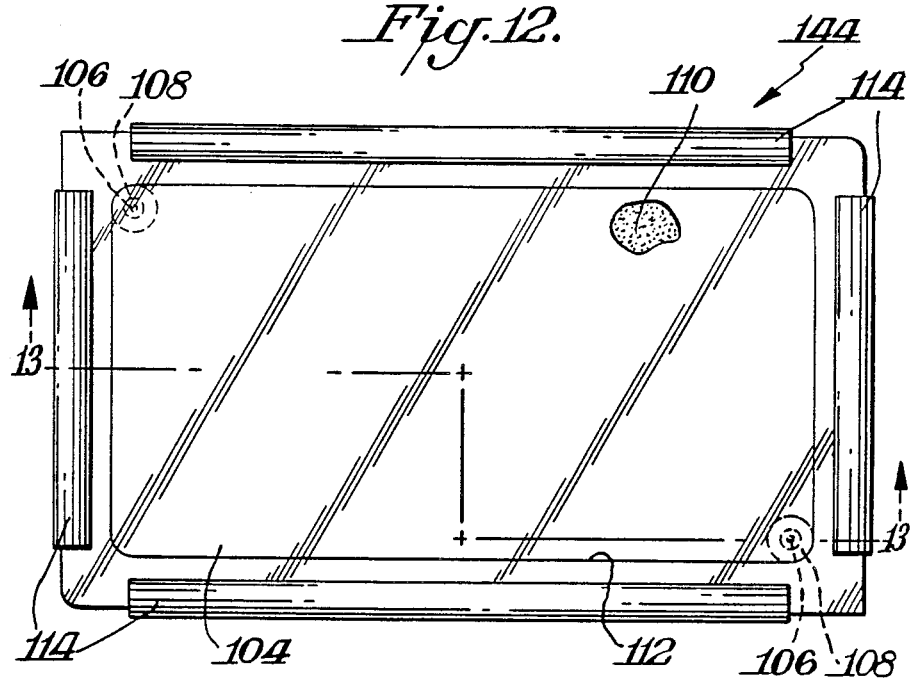
FIG. 12 is a top plan view of a gel mold and film support.
Figure 13:
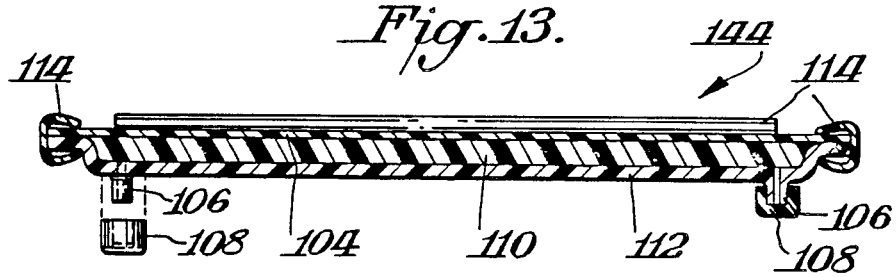
FIG. 13 is a cross-sectional view in elevation taken along line 13—13 of FIG. 12.

According to this invention the gel formulations are exposed in two part molds having a polystyrene tray 112 and having a polyester cover sheet 104 which serves as a gel support, as best seen in FIG. 13 and 15. A top view of FIG. 13 and 15 are seen in FIG. 12 and 14 respectively. The trays 112 are essentially shallow 4.5"×5" trays, 12 mils (300μ) deep and contain a series of ridges running about ¾ of the length of the gel dividing it into eight lanes. The trays 112 are covered with 7 mil "Gel Fix" polyester film 104 obtained from Serva Feinbiochemica to provide a flexible support for the completed electrophoresis gel. For special 2-D integrated gel application, electrodes to be printed on the support film. In this case the lane ridges and sample application wells are removed from the molds.

The polyester film 104 is sealed to the polystyrene tray 112 by applying a thin coating of Dow Corning silicone high vacuum grease to the edge of the mold and then rolling the two parts together. The grease provides a water-tight liquid seal. The two parts are then clamped together using strips of a plastic edge molding 114 for paper bundles (Slide-Lock Binding Bars) that are cut into strips the length of the gel. Following exposure, the gel adheres preferentially to the polyester film 104 support and thus can be pealed out of the mold due to the difference in adhesion between the two halves.

Uniform gel thickness is necessary to guarantee uniform electrophoretic migration across the gel. To insure uniform thickness during exposure, a 25 mil aluminum plate 102, cut to the dimensions of the gel mold, is placed over the polyester film 104. As best seen in FIGS. 14 and 15, exposure is made directly through this plate. This is possible with our system because of the high energy of the electron beam. However, the aluminum plate should not be required in other manufacturing schemes. Prior to attachment to the tray 112, the polyester film 104 is squeezed onto the plate 102 using water to provide adhesion. The laminate is then attached to the tray 112 using silicon grease and edge clamps as described earlier.

The trays 112 are filled through small ports 106 located at opposite corners of the tray 112. The trays 112 are held on an angle to allow air or argon to be displaced by the monomer solution. The ports 106 are capped with small rubber septa 108.

The mold assembly consisting of the gel formulation 110, polyester film 104, tray 112, edge molding 114, and aluminum plate 102 are placed on an aluminum support 113 to provide a rigid support for the tray 112. This device is termed the gel support assembly 144 and is used for gel polymerization regardless of the type of manufacturing process chosen.

Figure 17:
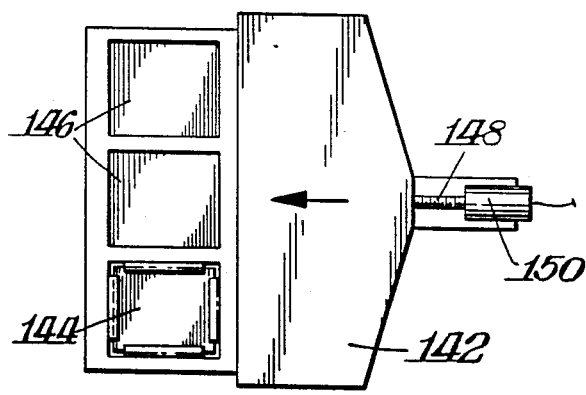
FIG. 17 is a drawing illustrating the top view of a shutter system for use in the manufacturing of electrophoretic gels.
Figure 16:
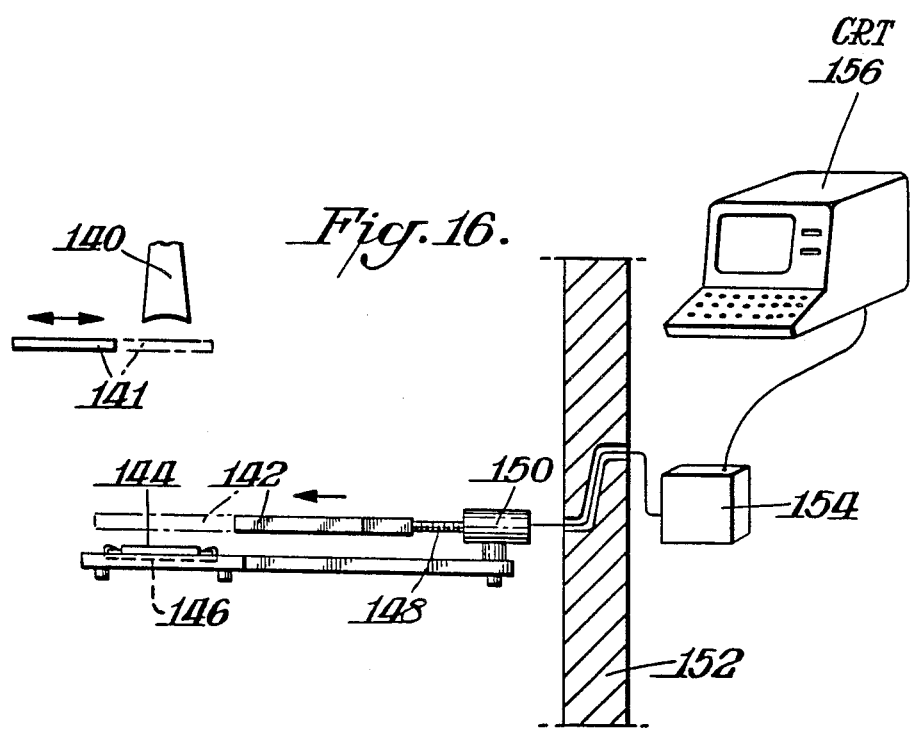
FIG. 16 is a drawing of a shutter system for use in the manufacturing of electrophoretic gels.

Illustrated in FIGS. 16 and 17 is a computer driven shutter device which is capable of producing dose gradients in a batch type mode. The programmable shutter 142 is placed at that distance below the source of ionizing radiation 140, which results in a uniform radiation distribution at the target. The gel support assemblies 144, filled with monomer as described, are then placed in the sample holders 146 in the upright position as best seen in FIG. 16, 2 or 3 abreast. The source of ionizing radiation is then activated by opening the beam shutter 141. Simultaneously the programmable shutter 142 is activated which starts to close via a screw drive 148 and stepper motor 150 arrangement controlled by the software commands of the computer 156 according to the desired dose profile. An Intel 8255A Programmable Peripheral interface 154 is used to coordinate the analog to digital control communications between the computer and shutter drive system. To isolate the user from high energy radiation, a radiation cell wall 152 made of suitable adsorption material is located between the shutter system and control room. A top view of this apparatus is illustrated in FIG. 17.

Figure 18:
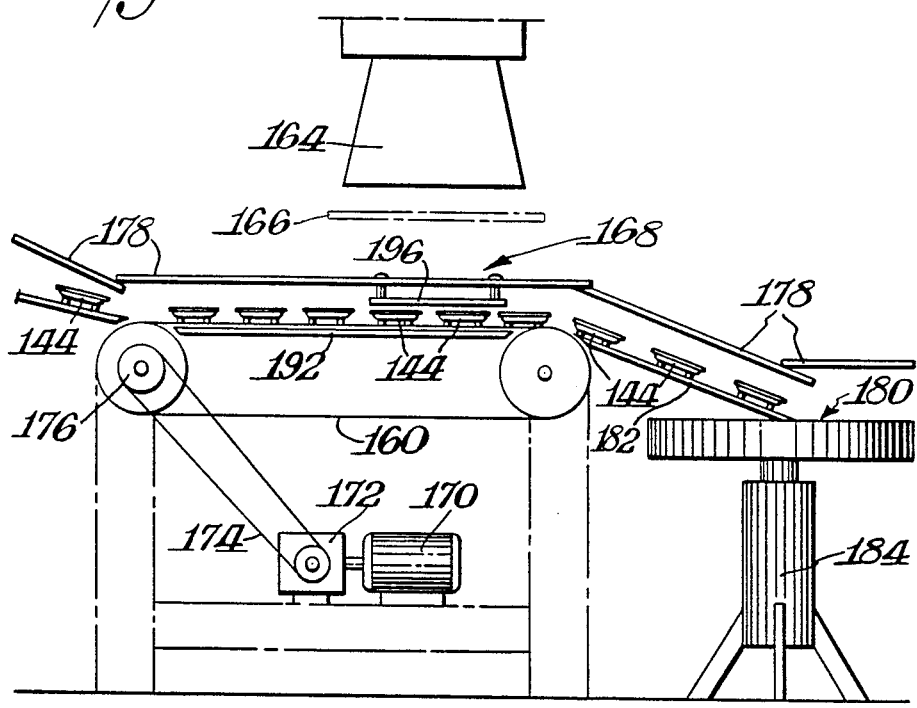
FIG. 18 is a drawing of a conveyor system for use in the manufacturing of electrophoretic gels.
Figure 19:
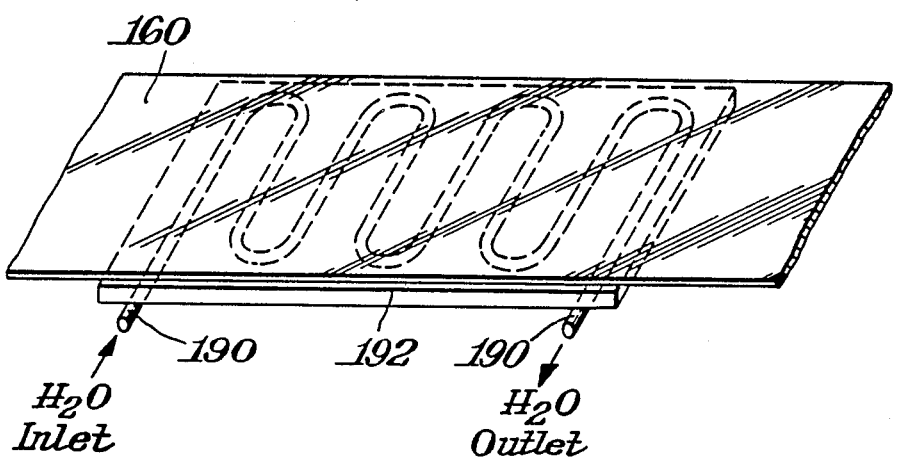
FIG. 19 is a drawing illustrating a device which is used to cool electrophoretic gels during irradiation.

A second device used for gel formulation exposure is a conveyor system for continuous manufacturing of gels, which is illustrated in FIG. 18. The gel support assemblies 144 are filled with monomer by hand and are then placed on a stainless steel conveyor belt 160, which is used to transport the gels to the source of ionizing radiation 164 and then on to the collection area 180. To help remove excess heat generated during irradiation, sample cooling is provided by circulating water through heat transfer tubes 190, which are attached to a back-up plate 192, which contacts the stainless steel belt 160 as illustrated in FIGS. 18 and 19.

After placing the gel support assemblies 144 on the conveyor belt 160, the source of ionizing radiation 164 is activated, and the beam shutter 166 is opened. When the beam has stabilized, the conveyor 160 is started and the gel support assemblies 144 pass under a slit, grid or screen assembly 168 at a constant predetermined belt speed, and accelerator beam current.

By knowing the calibrated accelerator dependent absorbed dose rate in samples of mass thickness (td) in Mrads/ma total accelerator beam current/sec from actinometry measurements, and selecting a desired dose rate for the gel samples in Mrads/sec, the accelerator beam current can be determined. With this information, knowing the relationship between limiting MW and dose or porosity and dose, a specific porosity can be produced by exposing a sample for a given length of time. Slit dimensions are normalized to a maximum dimension corresponding to maximum desired exposure. Knowing what this maximum exposure must be and the exposure dose rate, a belt speed can be calculated.

Figure 21:
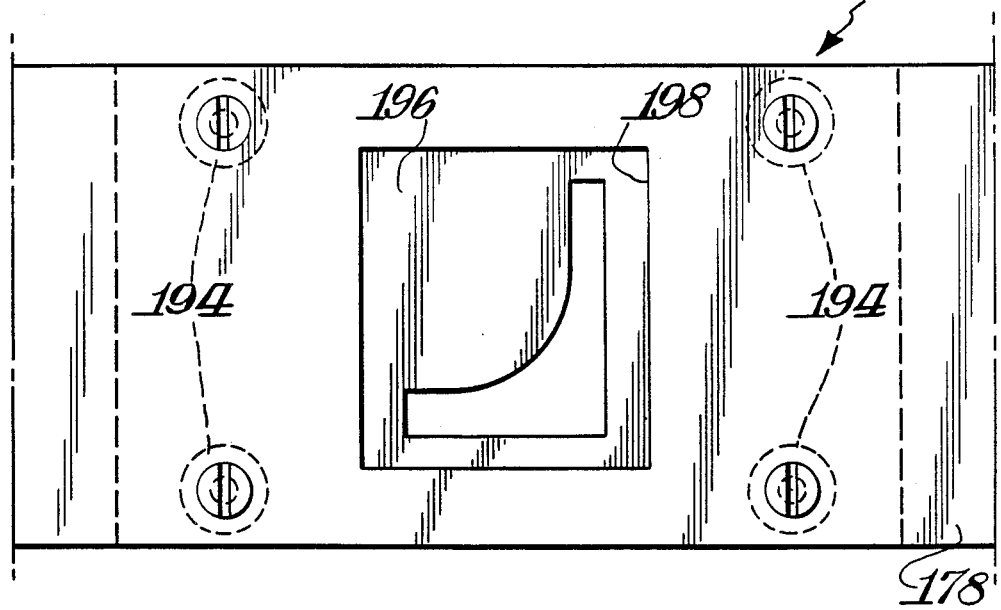
FIG. 21 is a drawing illustrating the top view of the slit shown in FIG. 20.
Figure 20:
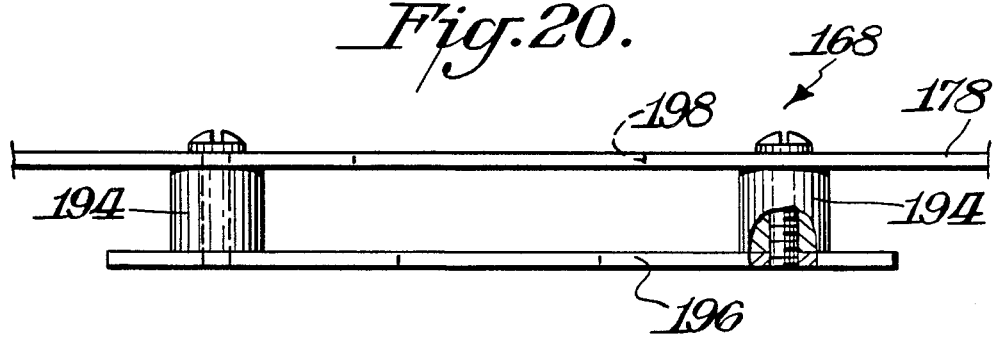
FIG. 20 is a drawing illustrating a typical slit, assembly used during gel irradiation.

An illustration of a typical slit, grid, or screen assembly 168 is shown in FIGS. 20 and 21. The slit mask 196 of interest is chosen depending upon the desired porosity profile required. The slit 196 is coupled to the holder and shield assembly 178, which acts as a retaining means for the electron filter of interest along with protecting the gel support assemblies 144 from unwanted radiation. To allow the passage of the ionizing radiation to the slit 196 a radiation window 198 is provided above the slit. The slit 196 is held parallel to the shield assembly 198 via four bushings 194.

The conveyor belt 160 (FIG. 18) is driven by a motor 170, which is coupled to a reduction gear box 172, which drives a belt 174, which in turn drives a belt pulley 176. During radiation the gel support assemblies 144 are protected from unwanted electron exposure by the shielding 178, which consists of aluminum or lead sheeting, located above the conveyor 160 and sample collection area 180. As the gel support assemblies 144 leave the conveyor 160 they slide down an exit ramp 182 into the sample storage area 180, which can be adjusted vertically by a hydraulic stand 184.

Since the electron accelerator produces a constant flux of electrons with constant energy over a defined area at a fixed rate, the dose given a specific area of the sample is directly proportional to the time of exposure. Time can be modulated by the programmed shutter movement, or by constant conveyor movement under variable fixed slits cut to dimensions corresponding to the desired gradient. Alternatively, sample exposure can be adjusted by modulating the relative amount of incident beam by passing it through a grid or halftone electron filter.

The calculations of slit dimensions, shutter movement, conveyor beltspeed, and accelerator beam current and effects resulting from differences in exposure dose rate on the gel porosity are all factors which must be determined prior to manufacturing electrophoretic gels using ionizing radiation.

Modifications can be made to the conveyor system to provide continuous introduction and removal of samples which are compatible with potential manufacturing processes.

An example of how each of the above manufacturing systems can be used to generate uniform porosity exposures, separate lane porosity variation exposures, and continuous gradient exposures is described below.

UNIFORM EXPOSURES

To produce a uniform exposure using the batch type shutter system (See FIG. 16), the samples 144 are placed on the shutter table 146 so that each portion of the gel 144 is exposed for the same length of time. In the conveyor system FIG. 18, the samples 144 are passed under a square or rectangular slit 196 at constant rate. These two manufacturing methods are subtly different from each other even though they both produce the same overall dose. With the shutter system, the sample 144 receives essentially a uniform instantaneous exposure over its entire surface area simultaneously initiating polymerization at all points in the gel. With the conveyor system a radiation front passes over the gel producing a corresponding polymerization or reaction front, along with its associated diffusion and thermal gradients. Under the manufacturing condition disclosed, no differences are observed in the resultant gels.

LANE EXPOSURES

To produce a gel with separate lanes having different but uniform exposures using a batch type system (See FIGS. 16 & 17) requires the manual or automatic movement of the shutter 142 across the length of the gel in a stepped fashion to mask the sample in an exposure pattern similar to the one described in FIGS. 7 & 8. The preferred method of producing "lane" exposures is the use of the conveyor system, FIG. 18, with a slit pattern the same as that described in FIG. 7.

CONTINUOUS GRADIENT EXPOSURES

The final kind of exposure used was one to produce dose gradients corresponding to a specific desired porosity range or limiting molecular weight distribution along the length of the gel in the electrophoresis direction. These gradients were produced using both shutter and variable fixed slits with the conveyor. The use of each will be described.

Using the batch type shutter system, FIGS. 16 and 17, the shutter 142 is opened to its maximum position and the gel 144 positioned in the table 146 with the electrophoresis direction perpendicular to the edge of the shutter 142. The ionizing radiation source is started, and the beam shutter 141 is opened. Simultaneously the sample shutter 142 is activated to close at a programmed rate to give the desired dose profile.

The preferred means of exposure is using the conveyor system (FIG. 18), with the use of masks 168 to produce the gradient. The masks 168 are cut in specific patterns required to produce the dose gradients needed to generate particular molecular weight or porosity versus distance profiles. Sample gels 144 are placed on the conveyor with the electrophoresis direction perpendicular to the direction of the belt movement and then irradiated. FIGS. 9a–d illustrates different representative mask patterns available to give desired electrophoretic porosity responses.

Figure 22:
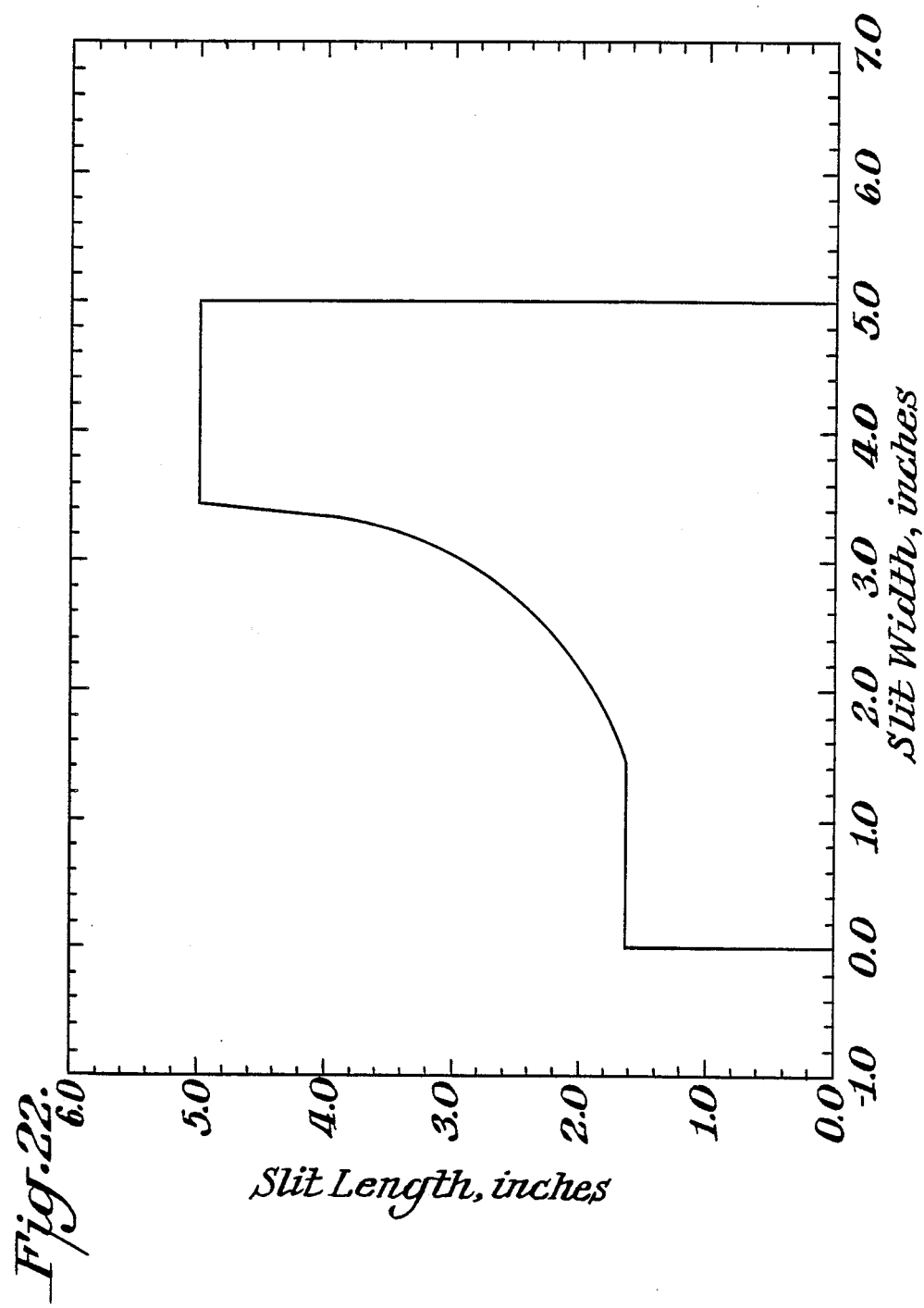
FIG. 22 is a drawing illustrating a slit profile which yields a linear MW versus distance porosity profile.
Figure 23:
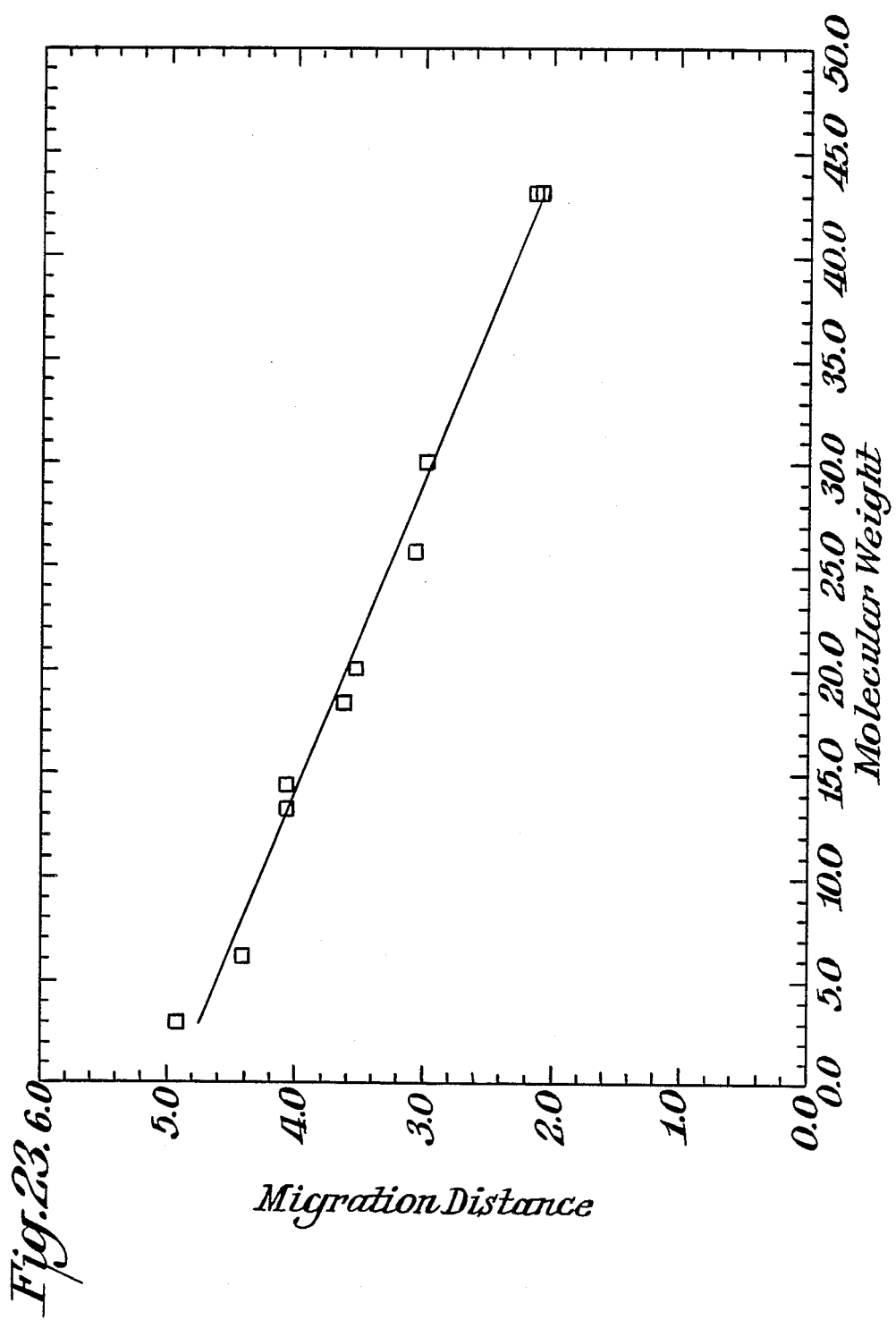
FIG. 23 is a drawing illustrating the migration distance versus the linear molecular weight which results from the dose profile created by the slit in FIG. 22.
Figure 24:
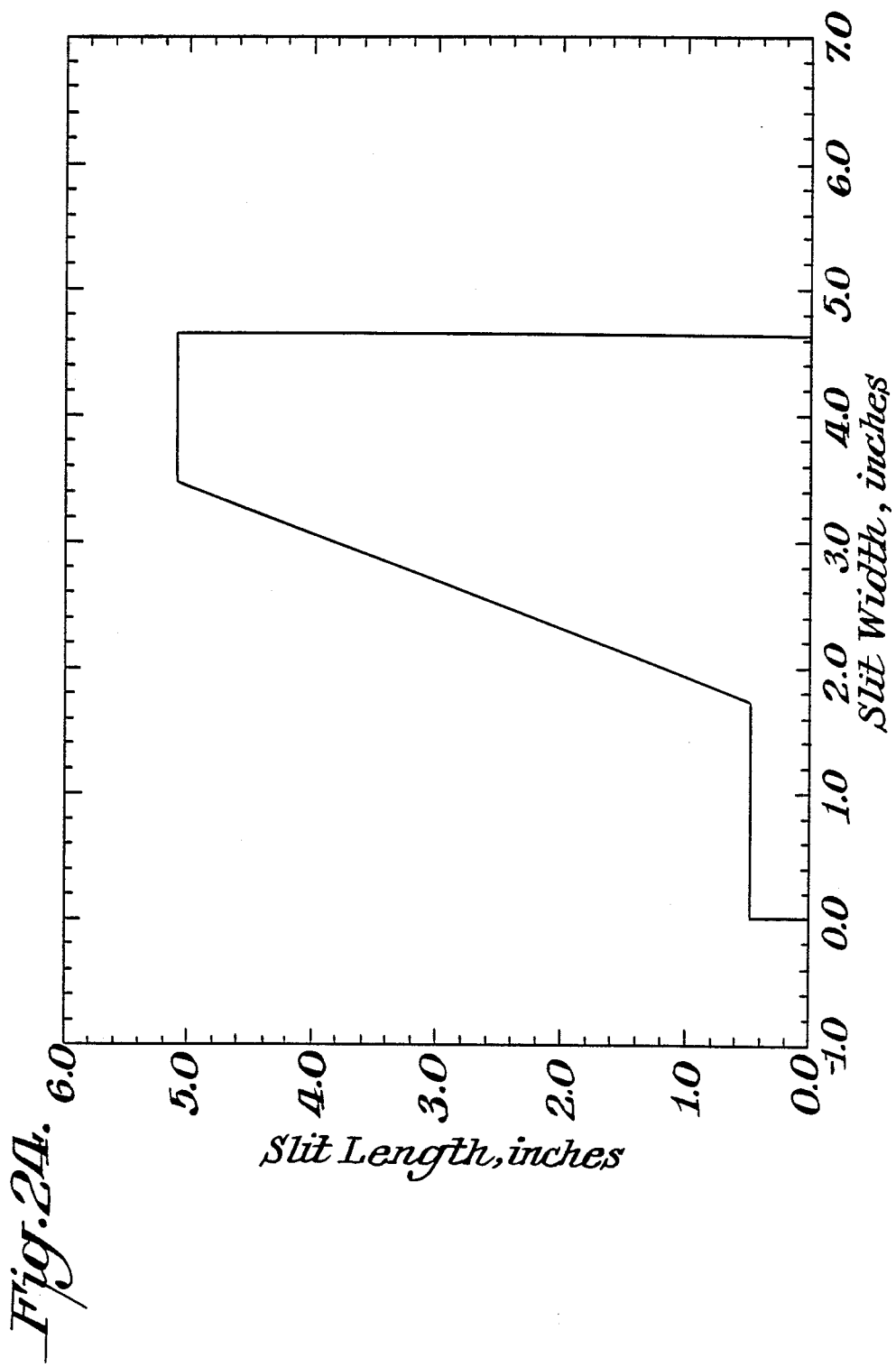
FIG. 24 is a drawing illustrating a slit profile which yields a log (MW) versus distance porosity gradient.
Figure 25:
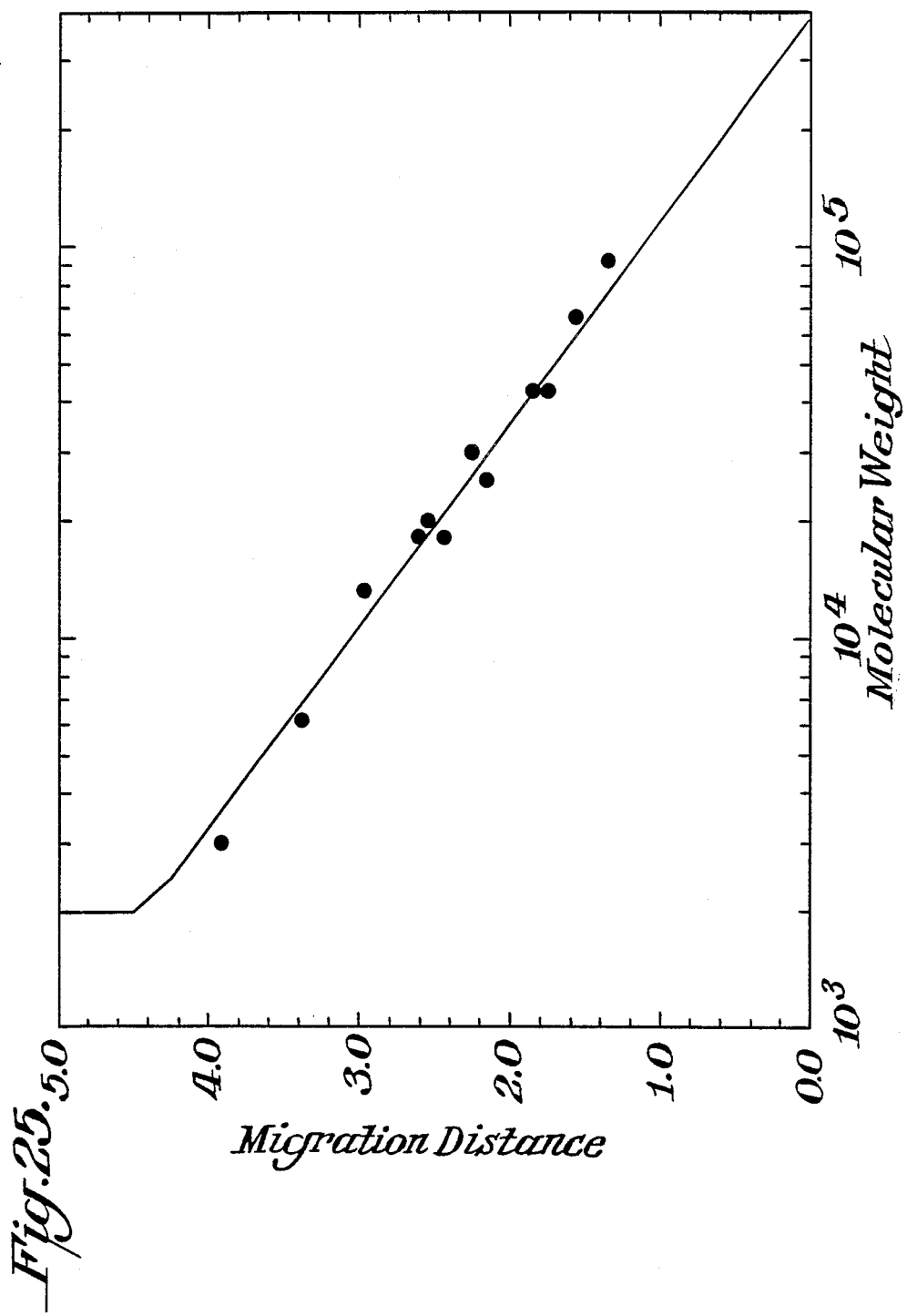
FIG. 25 is a drawing illustrating the migration distance versus log (MW) which results from the dose profile created by the slit in FIG. 24.

Illustrated in FIG. 22 is a representation of a dose profile which yields a linear MW versus distance distribution, the results of which is illustrated in FIG. 23. Illustrated in FIG. 24 is a representation of a dose profile which yields a log MW versus distance curve, the results of which is illustrated in FIG. 25. In the figures representing the protein migration distance, the solid lines represent the theoretical predicted position for proteins at their exclusion limit. The symbols represent actual data sets of protein migratory distance.

COATING PROCEDURE

While a casting procedure using molds must be used for making gels form pure water/monomer formulations, a continuous coating procedure can be used with solutions that have been thickened using either polyacrylamide or some other compatible, water soluble polymers. Two possible coating techniques will be described. The first utilizes a cover sheet, the second an inert coating-reaction chamber.

Figure 28:
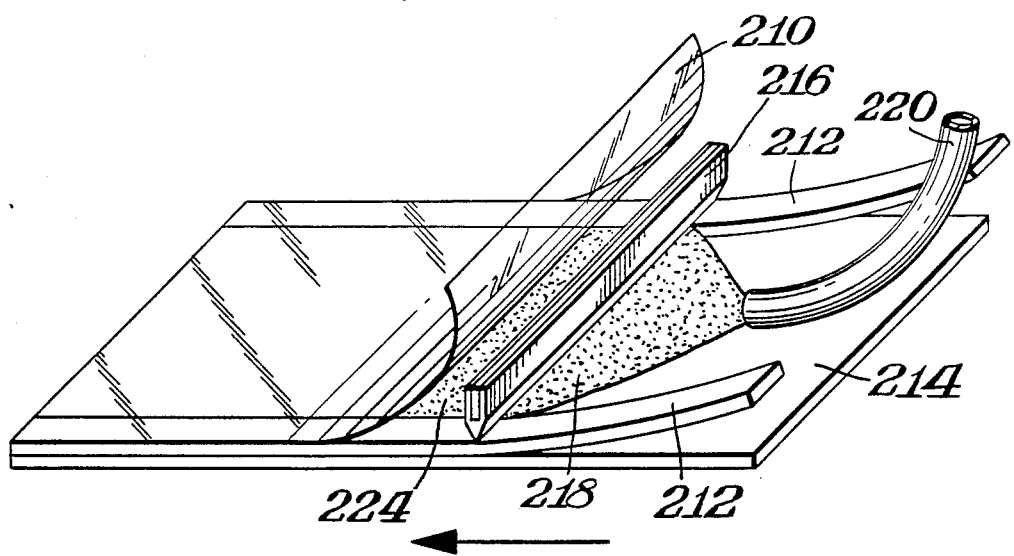
FIG. 28 is a drawing illustrating a continuous coating procedure utilizing a cover sheet.

If the gel formulations are coated at a remote location from the radiation source, a cover sheet 210 as best seen in FIG. 28, will have to be applied to prevent evaporation of solvent (water) and provide an oxygen barrier for polymerization. The cover sheet 210 may also contain printed electrodes and the like, or these may be included as part of the base. To provide uniform gel thickness, spacers 212 must be used. These are placed on the film support 214 as a template. The monomer-polymer composition 218 is then pumped onto the film support 214 by way of a nozzle 220. A coating knife 216 is used to form the monomer-polymer formulation 218 into a uniform gel.

Figure 29:
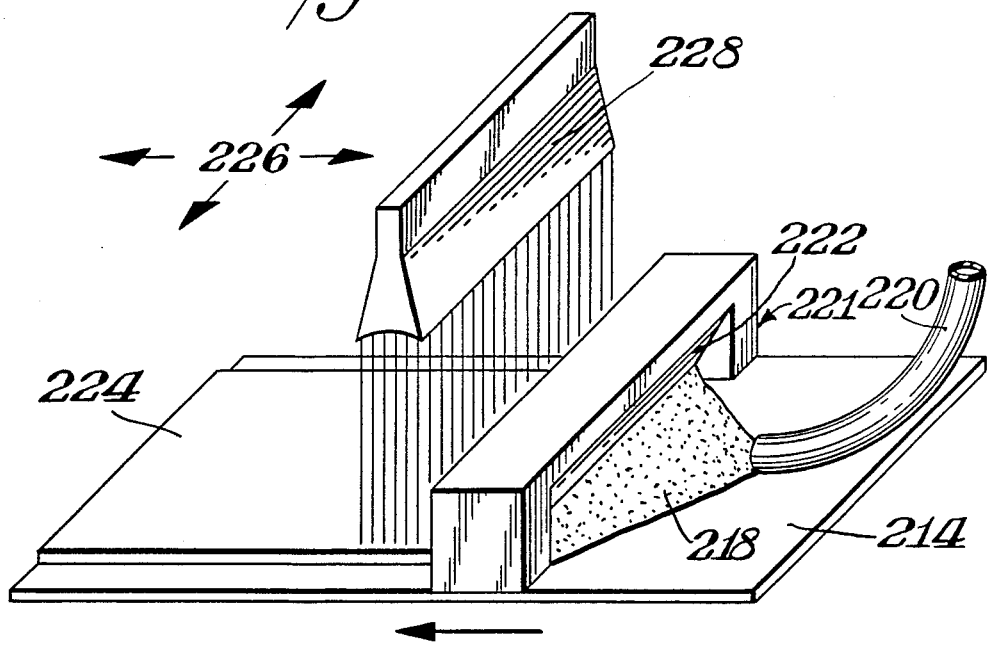
FIG. 29 is a drawing illustrating a continuous coating and polymerization procedure utilizing an inert coating-radiation chamber.

If the monomer-polymer composition has sufficient physical integrity, a coating of predetermined thickness can be made using a doctor knife 222, which is housed in a U-shaped bracket which provides support during gel manufacturing as best seen in FIG. 29. As in FIG. 28, the monomer-polymer composition 218 is pumped by way of a nozzle 220 onto the film support 214. The gel is then formed via the doctor knife 222 and then polymerized by the radiation source 228, in an inert atmosphere 226. Temperature and humidity must be regulated to prevent solvent loss during coating and irradiation. Both of the methods described above can be used for irradiating thickened monomer solutions or pure water soluble polymer solutions to produce a given gel product 224.

MONOMER CONVERSION IN GEL MATERIALS

The toxicity of acrylamide monomer is well established. It is therefore desirable to produce gel materials with low residual monomer content. We have established that the residual acrylamide content in radiation polymerized and conventional chemical polymerized gels is essentially equivalent for IEF and uniform PAGE gel materials. However, radiation produced gradient gels may contain higher residual monomer in porous regions of the gradient. Stability studies have shown, however, that this does not effect the electrophoretic performance or stability of the gel materials.

Analysis of the interaction of formulation and electron exposure on gel porosity suggests several approaches by which the residual monomer content in the electron beam gradient gels can be reduced or eliminated. These include:

Use radiative cross-linking to control the restrictive properties of the gel;

Manipulation of electron dose rate to control polymer molecular weight;

Replacement of acrylamide with an acrylamide prepolymer; and

Substitution of acrylamide with non-toxic high molecular weight oligomer monomers.

Radiative cross-linking is an attractive approach for reducing the residual monomer content in gels. This is based on our findings that (a) radiative cross-linking requires higher doses of electrons than direct polymerization and (b) that interaction of bisacrylamide with electron produced polymer radicals leads to branching and cross-linking which enhances the restrictive properties of the gel. By reducing the bis-acrylamide content in the gel formulation and extending the electron exposure to maximize radiative cross-linking. It is theorized that a higher proportion of the acrylamide monomer could be consumed early in the polymerization process without substantially increasing the porosity of the gel. The restrictive properties of the gel could then be increased by increasing the degree of radiative cross-linking.

Figure 26:
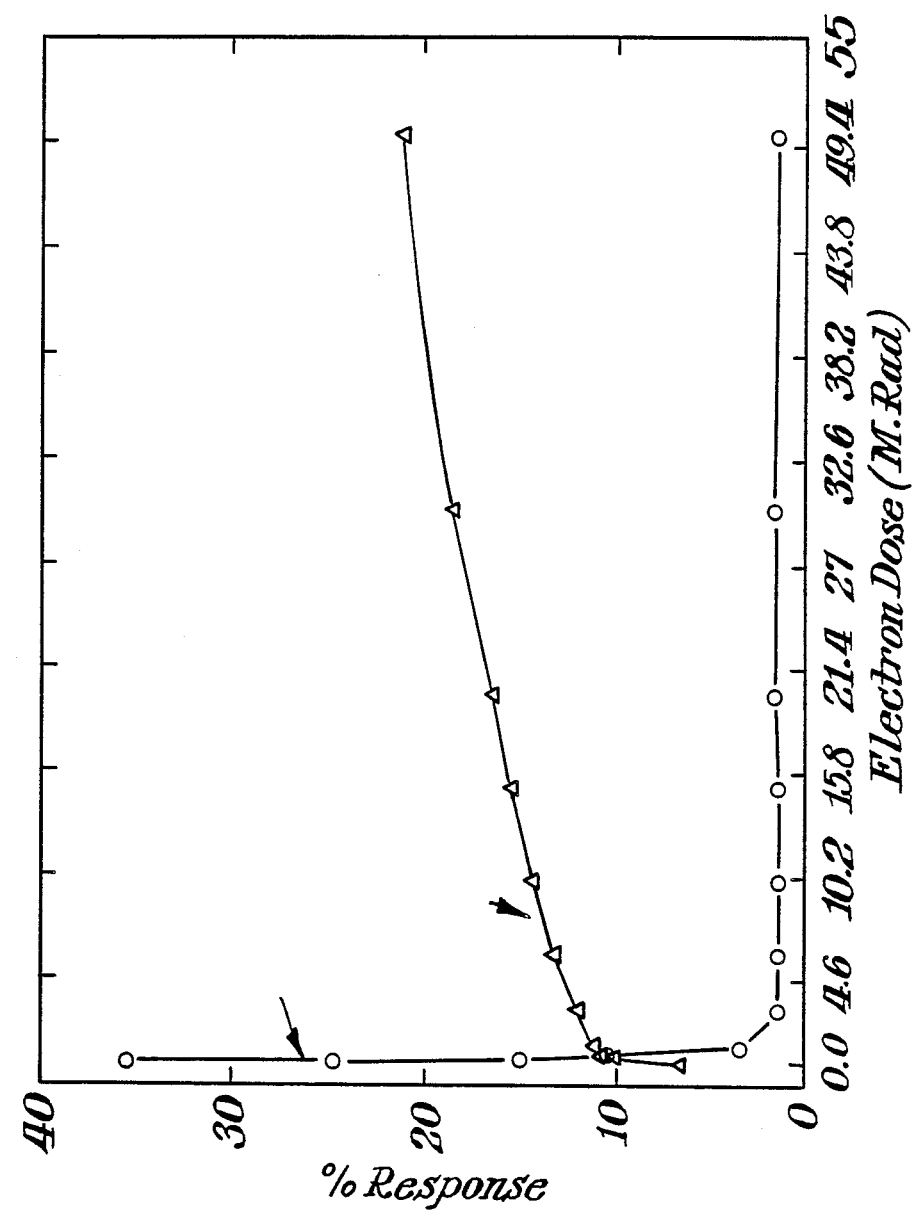
FIG. 26 is a drawing illustrating the percent residual monomer and gel porosity as a function of electron dose for a 20T, 1C Gel at 0.01 Mrad/sec.
Figure 27:
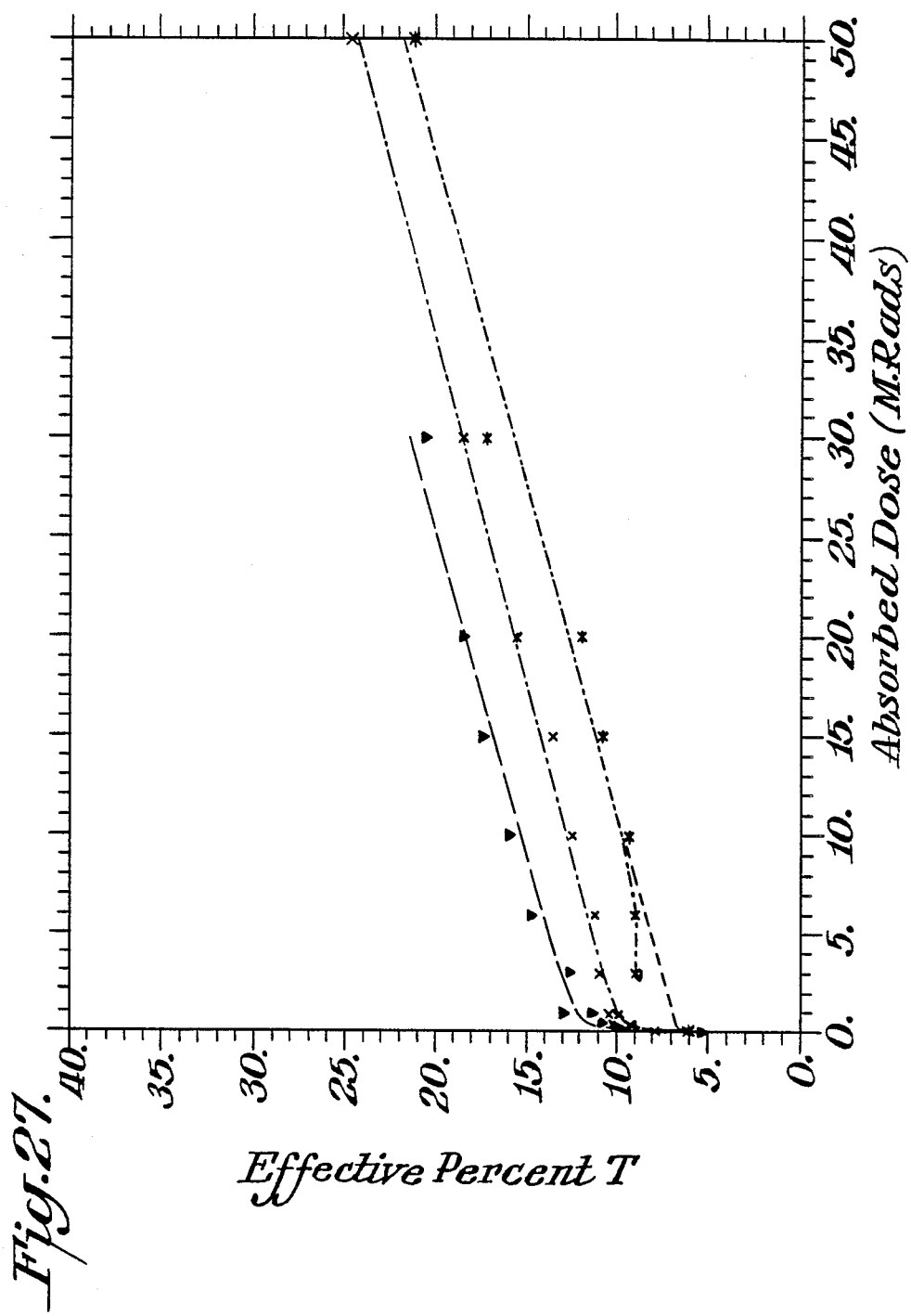
FIG. 27 is a drawing illustrating the effective percent T versus the adsorbed Dose for a 20T, 0C, 20T, 0.5C, and 20T, 1C Gels.

To demonstrate this approach, gels were prepared with reduced bisacrylamide concentrations (0.5, 1% C). The gel formulations were then given an expanded range (0.05 to 50 Mrads) of electron exposure. The gel porosity was then evaluated using electrophoretic separation of mixtures of standard proteins. Residual monomer content was measured by HPLC. As shown in FIGS. 26 and 27, the gels prepared with reduced bis (1% C) display both a substantial reduction in the residual monomer content and a useful range (6-23%) of gel porosity. These findings indicate that by manipulating the concentration of cross-linker monomer and the extent of electron exposure, gels can be produced with both a wide range of porosities and a high degree of monomer conversion.

The other approaches mentioned above appear attractive as means of reducing the monomer content throughout the entire gradient gel. We have shown that the dose rate is an important variable influencing the extent of polymerization and thus the molecular restrictive properties of the gel. In general, gels produced at higher dose rates tend to be less restrictive than gels given the same total exposure at lower dose rates. At higher dose rates, monomer may be effectively consumed without producing highly restrictive gels.

These observations can be used to advantage to control the residual monomer content in pore gradient gels. Specifically by varying the dose rate during the course of gel exposure, gels may be produced with essentially complete monomer consumption but with a wide range of gel porosity.

Furthermore, by replacing acrylamide with non-toxic prepolymerized acrylamide or acrylamide oligomers, the acrylamide toxicity in electrophoretic gels can be essentially eliminated.

DIRECT PRODUCTION OF GELS BY RADIATIVE CROSS-LINKING OF WATER SOLUBLE POLYMERS

Aqueous solutions of water soluble polymers may be irradiated to form restrictive gel networks directly. This network is produced by radiation induced cross-links on polymer molecules, as illustrated in FIGS. 26 and 27. As seen in FIG. 26, representing a 20 T, 1 C gel composition, essentially all free monomer is consumed within the first Mrad of exposure. A rapid increase in gel restrictiveness accompanies the decrease in monomer corresponding to polymerization and accompanying direct cross-linking of the composition through the combination of BIS cross-linkers and radiative cross-linking. After all monomer has been consumed the restrictiveness of the gel is seen to continue to increase linearly as a function of dose. This corresponds to direct radiative cross-linking of the matrix. This response is further demonstrated by the data plotted in FIG. 27. In each case, essentially all monomer was consumed with less than 1 Mrad exposure. The gels become more restrictive at higher doses. The bottom curve corresponds to the change in porosity of linear polyacrylamide, a typical water soluble polymer. It is seen that a 20% T solution of polyacrylamide has the restrictive properties of a typical "6.5% T Gel." This porosity value is probably a measure of the torturous path through which the proteins must migrate. The different curves in FIG. 27 represent compositions with differing amounts of bis-cross-linkers added to the initial formulation and show the effect of chemical cross-linker on gel restrictiveness during the initial polymerization stage. Radiative cross-linking generally increases the restrictive properties of the gel as a function of dose for each set of formulations beyond that which can be achieved by chemical induced polymerization. It should be noted that there is a synergistic effect between radiative and chemical cross-linking during the early polymerization stage which results from reaction of radiation induced polymer radicals and pendent olefin groups from incorporated BIS molecules. It is also seen from both figures that direct radiative cross-linking can extend the restrictiveness of the gel beyond the maximum attainable by normal chemical means.

As has been demonstrated here with polyacrylamide, restrictive gel networks also can be produced by irradiating aqueous solutions of other water soluble polymers. Solutions containing 10% to 30% polyvinylpyrrolidone, polyacrylic acid, polyvinylalcohol and polymethylvinylether have been given from 1 to 50 Mrads exposures to produce insoluble gels. The response of these systems to radiation is dependent on the chemical nature of the dissolved polymer, some being significantly more sensitive than others to radiation. Other water soluble polymers than those listed may be expected to respond similarly.

GEL PRODUCTS 100

Using this invention to induce electrophoretic gel polymerization via ionizing radiation it is possible to electrophoretically separate bioorganic molecules using the gel products 100 set forth in the above disclosure by the steps of placing a sample of bioorganic molecules on a thin plate of the gel product and applying a voltage across a dimension other than the thin dimension of the plate. The gel products may vary in thickness from $50\mu$ to 2 mm with the $100-300\mu$ range being most preferred. Also, depending upon the desired electrophoretic separation required, the gels may be designed for specific molecular weight or porosity versus distance distributions across a gel or have uniform, lane, or gradient porosity profiles. The advantages of electron beam polymerized gels are summarized as follows:

ACCURATE AND REPRODUCABLE GELS

The precise control of sample formulation and preparation, electron flux and sample placement affords excellent reproducability in gel preparation. This translates into high reproducibility of gradient shape and type. To confirm this a series of 116 gels were prepared in three different lots and exposed on three different days. Gradient exposures were made using the computer programmed shutter (See FIG. 16). Expected error was introduced in sample preparation of different lots, positioning and activation of the shutter, sample to sample variation in electrophoresis conditions and in precise measurement of protein/tracker dye positions. The results from this series of experiments are shown in Example #6.

In spite of the many possible sources of error, the standard deviation of all proteins in all lots and in the combined set are essentially identical and equal to 0.02. The error in protein position for the 116 points is ±0.6%. The increase in CV (coefficient of variation) as the protein molecular weight is increased from 3000 to 25700 coupled with constant SD indicates that the primary source of error in the experiment is in precise measurement of protein band position and not related to any chemical or structural variation between gels.

EXAMPLE 6

| | Reproducibility Statistical Summary | | | | | |
|---|---|---|---|---|---|---|
| | Protein | | | | | |
| MW→ | $P_1$ 3000 | $P_2$ 6200 | $P_3$ 13300 | $P_4$ 18400 | $P_5$ 25700 | Ave. |
| Set #1 | | | | | | |
| # of Points, DF | 28, 27 | 28, 27 | 28, 27 | 28, 27 | 28, 27 | 28, 27 |
| Confidence Level | 95 | 95 | 95 | 95 | 95 | 95 |
| T value | 2.052 | | | | | 2.052 |
| Mean | 0.880 | 0.786 | 0.710 | 0.645 | 0.573 | 0.719 |
| SD | 0.021 | 0.021 | 0.019 | 0.020 | 0.021 | 0.020 |
| CV | 0.024 | 0.027 | 0.027 | 0.031 | 0.036 | 0.029 |
| ±Range | 0.008 | 0.008 | 0.007 | 0.007 | 0.008 | 0.008 |
| | | | | | | (0.011) = |
| | | | | | 163 | |
| | | | | | 0.008 | |
| | | | | | | 0.719 |
| Set #2 | | | | | | |
| # of Points, DF | 44, 43 | | | | | 44, 43 |
| Confidence Level | 95 | | | | | 95 |
| T value | 2.021 | | | | | 2.021 |
| Mean | 0.887 | 0.789 | 0.712 | 0.648 | 0.559 | 0.719 |

EXAMPLE 6-continued

Reproducibility Statistical Summary

| MW→ | P$_1$ 3000 | P$_2$ 6200 | P$_3$ 13300 | P$_4$ 18400 | P$_5$ 25700 | Ave. |
|---|---|---|---|---|---|---|
| SD | 0.023 | 0.026 | 0.028 | 0.030 | 0.032 | 0.028 |
| CV | 0.026 | 0.033 | 0.039 | 0.047 | 0.058 | 0.041 |
| ±Range | 0.007 | 0.007 | 0.008 | 0.009 | 0.009 | 0.008 |
| | | | | | | (0.012) = |
| | | | | | | 0.008 |
| | | | | | | 0.719 |
| Set #3 | | | | | | |
| # of Points, DF | 44, 43 | | | | | 44, 43 |
| Confidence Level | 95 | | | | | 95 |
| T value | 2.021 | | | | | 2.021 |
| Mean | 0.878 | 0.780 | 0.702 | 0.635 | 0.548 | 0.709 |
| SD | 0.017 | 0.015 | 0.016 | 0.019 | 0.018 | 0.017 |
| CV | 0.019 | 0.019 | 0.022 | 0.030 | 0.033 | 0.025 |
| ±Range | 0.005 | 0.004 | 0.004 | 0.005 | 0.005 | 0.005 |
| | | | | | | (0.007) = |
| | | | | | | 0.005 |
| | | | | | | 0.709 |
| Set #4 | | | | | | |
| # of Points, DF | 116, 115 | | | | | 116, 115 |
| Confidence Level | 95 | | | | | 95 |
| T value | 1.98 | | | | | 1.98 |
| Mean | 0.088 | 0.785 | 0.708 | 0.642 | 0.558 | 0.715 |
| SD | 0.021 | 0.021 | O.022 | 0.025 | 0.026 | 0.023 |
| CV | 0.023 | 0.027 | 0.031 | 0.038 | 0.046 | 0.033 |
| ±Range | 0.003 | 0.003 | 0.004 | 0.004 | 0.004 | 0.004 |
| | | | | | | (0.006) = |
| | | | | | | 0.004 |
| | | | | | | 0.715 |

Variation Between Gels = ± 0.602%

CUSTOM GELS

Gel gradients may be customized to any pattern porosity profile through microprocessor control of beam, shutter, slit or mask. For example, discontinuous gradients and gradients of complex profiles can be readily produced.

CLEANER GELS

Absence of chemical initiator obviates potential reaction with protein samples and can reduce background staining. Separation is sharper and stained protein spots show higher contrast with background.

CONTINUOUS PRODUCTION OF GELS

Currently, gels are batch prepared. The instant case allows continuous production. Each gel can thus be made rapidly under reproducable conditions.

THINNER GELS

The radiation polymerization process enables the production of thin gradient gels (500μ) which are not readily produced by conventional processes. Since thin gels require less power to run they can be electrophoresed faster and are easier to handle. This is faster and saves energy.

REDUCED ENDOSMOSIS FLOW

The degree of electroendosmosis flow in the gel can be reduced due to the reduced ionic content of the gel formulation.

IEF GELS

Normal gels as prepared in the art have organic bases, such as tetramethylenediamine (TMEDA) present as polymerization catalysts. For IEF applications, such bases can migrate and distort local pH values in the overall pH gradient. Their absence in the instant case means more stable, accurate pH gradients as well.

SAFER GELS

Since the user does not have to handle toxic acrylamide, the packaged gel materials can be more safely handled.

FASTER MIGRATION IN IEF GELS

The absence of ionic initiators and hydrogen donors reduces the ionic content of the gel material. This allows higher voltages to be applied to the gel with reduced heat production.

STABLE GRADIENT

Unreacted initiators in other systems may cause polymerization of free monomer or cross-linking of polymer to occur after gel preparation is complete. Thus cross-link density and gradient can change uncontrollably. Absence of initiators stabilizes the gradient.

EXTENDED SHELF LIFE

Absence of thermal or photochemical, radical initiators potentially eliminates possible random reaction of initiator with free monomer, buffers, solvents, or acrylamide polymer.

What is claimed is:

1. A method of electrophoretically separating bioorganic molecules using a porous electrophoretic gel product comprising an aqueous-swelled porous polymer matrix formed of homo- or co-polymers which defines a volume, the polymer matrix being formed from water soluble, ethylenically unsaturated monomers which can undergo ionizing radiation initiated polymerization, the product characterized by having a constant atomic composition over its volume, an absence of a polymerization catalyst, being stable, having a controlled electrophoretic resolving capacity that is responsible from gel to gel for the electrophoretic separation of charged macromolecular substances, having length, width and thickness dimensions, and having a porosity gradient along one of the length and width dimensions and uniform porosity along the thickness dimension which dimension is relatively thin, by the steps of placing a sample of bioorganic molecules on the gel product, and applying a voltage across a dimension other than the thickness dimension.

2. A method of electrophoretically separating bioorganic molecules using the gel product set forth in claim 1 wherein the acrylamide monomers consist essentially of from about 3% weight/volume to about 30% weight/volume.

3. The gel product set forth in claim 2 wherein the porosity gradient is represented by a mathematical function.

4. The gel product set forth in claim 3 wherein the porosity gradient in one of the length and width dimensions is discontinuous.

5. The gel product set forth in claim 3 wherein the porosity gradient in one of the length and width dimensions is logarithmic.

* * * * *